(12) United States Patent
Demizu et al.

(10) Patent No.: US 11,103,688 B2
(45) Date of Patent: Aug. 31, 2021

(54) TUBE JOINING DEVICE

(71) Applicant: TERUMO KABUSHIKI KAISHA, Tokyo (JP)

(72) Inventors: Shun Demizu, Kanagawa (JP); Tomotaka Kokubu, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 4 days.

(21) Appl. No.: 16/632,655

(22) PCT Filed: Mar. 26, 2018

(86) PCT No.: PCT/JP2018/012083
§ 371 (c)(1),
(2) Date: Jan. 21, 2020

(87) PCT Pub. No.: WO2019/021529
PCT Pub. Date: Jan. 31, 2019

(65) Prior Publication Data
US 2020/0164197 A1  May 28, 2020

(30) Foreign Application Priority Data
Jul. 24, 2017 (JP) .............................. JP2017-142857

(51) Int. Cl.
*A61M 1/28* (2006.01)
*A61M 39/14* (2006.01)
(Continued)

(52) U.S. Cl.
CPC ............ *A61M 39/146* (2013.01); *A61M 1/28* (2013.01); *B29C 66/5221* (2013.01);
(Continued)

(58) Field of Classification Search
CPC ...... A61M 1/28; A61M 39/146; A61M 39/18; A61M 2205/14; A61M 2207/10; B29C 65/18; B29C 65/20; B29C 65/203; B29C 65/2046; B29C 65/2061; B29C 65/2076; B29C 65/743; B29C 65/7802; B29C 65/7841; B29C 66/0018; B29C 66/002;
(Continued)

(56) References Cited

U.S. PATENT DOCUMENTS 5,802,689 A * 9/1998 Sano .................... B29C 66/1142
29/33 T
7,119,305 B2 * 10/2006 Sano .................... B29C 65/203
219/243

FOREIGN PATENT DOCUMENTS

JP 2016022227 A * 2/2016 ......... B29C 66/1142
JP 2016022227 A 2/2016

* cited by examiner

*Primary Examiner* — Michael A Tolin
(74) *Attorney, Agent, or Firm* — Terumo BCT, Inc IP Law Dept.

(57) ABSTRACT

Provided is a tube joining apparatus that allows a user to easily and properly set tubes to be joined, and can prevent occurrence of joining failures due to tube setting errors. A tube joining apparatus 1 includes a housing 10, a lid 22 relatively movable toward and away from the housing, a tube holding part 23 that holds a first tube T1 and a second tube T2 individually in a state of being placed side by side in an oblique direction D1 with respect to a height direction Z of the housing, and a tube pressing part 25 that presses the first tube and the second tube against each other as the lid relatively moves toward the housing.

16 Claims, 15 Drawing Sheets

(51) Int. Cl.
  *B29C 65/20*   (2006.01)
  *B29C 65/00*   (2006.01)
  *B29L 23/00*   (2006.01)

(52) U.S. Cl.
  CPC ....... *B29C 66/857* (2013.01); *A61M 2207/10* (2013.01); *B29L 2023/007* (2013.01); *B29L 2023/22* (2013.01)

(58) Field of Classification Search
  CPC . B29C 66/1142; B29C 66/5221; B29C 66/71; B29C 66/7373; B29C 66/73921; B29C 66/816; B29C 66/8167; B29C 66/8221; B29C 66/857; B29C 66/8618; B29C 66/8746; B29C 66/91921; B29K 2027/06; B29L 2023/007; B29L 2023/22
  See application file for complete search history.

TUBE JOINING DEVICE

TECHNICAL FIELD

The present invention relates to a tube joining apparatus used to join tubes.

BACKGROUND ART

As a technique for joining resin tubes or the like together, there is a conventionally known joining method in which end portions of resin tubes are cut by melting, and the cut ends are pressed against each other to be pressure-joined. This technique is widely used in various industrial fields. As an example, its application to medical technology such as peritoneal dialysis has been attempted.

Peritoneal dialysis is a method in which a tube (catheter) implanted in the abdominal cavity of a patient is used to introduce a predetermined dialysate into the body, and then water and waste products transferred into the dialysate through the peritoneum is removed out of the body. When the dialysate is introduced into the body, the tube implanted in the patient is liquid-tightly joined to a tube of a bag containing the dialysate. When the dialysate is drained from the body, the tube implanted in the patient is liquid-tightly joined to a tube of a drain bag.

Since one tube to be joined is implanted in the abdominal cavity of the patient as described above, close attention must be paid to a joining operation so that the tubes are not contaminated during the operation. In view of this point, as described in Patent Literature 1, for example, a tube joining apparatus has been developed which enables cutting of two resin tubes by melting and automatically joining them under aseptic conditions. This apparatus exchanges the positions of cut end portions of the two tubes and joins the tubes, and thus ends concern over bacterial contamination during joining, and can keep a dialysate or the like in the tubes and a bag sterile. In this apparatus, the two tubes are placed on each other in close contact in a vertical direction (height direction) of the apparatus, and a heated plate-shaped metal wafer is moved toward the tubes to cut them by melting.

CITATION LIST

Patent Literature

Patent Literature 1: JP 2013-146354 A

SUMMARY OF INVENTION

Technical Problem

When using the above-described tube joining apparatus, a user such as a patient manually sets tubes to be joined in the tube joining apparatus, placing them on each other in the height direction of the apparatus. At this time, the user may mishandle the tubes, placing the tubes on each other in a twisted state or placing them on each other in three layers because the tubes themselves have flexibility. If the apparatus is caused to perform a cutting and joining operation with the tubes set like this, the tubes are joined to each other, but a joining failure such as a hole formed in a joined portion occurs.

The present invention has been made in view of the above problem, and its object is to provide a tube joining apparatus that allows a user to easily and properly set tubes to be joined, and can prevent occurrence of joining failures due to tube setting errors.

Solution to Problem

A tube joining apparatus according to the present invention that solves the above problem is a tube joining apparatus that melts and cuts an end portion of a first tube and an end portion of a second tube with a heated plate-shaped cutting member, and then exchanges positions of the cut end portion of the first tube and the cut end portion of the second tube and joins the tubes under aseptic conditions. The tube joining apparatus includes a housing, a lid relatively movable toward and away from the housing, a tube holding part that holds the first tube and the second tube individually in a state of being placed side by side in an oblique direction with respect to a height direction of the housing, and a tube pressing part that presses the first tube and the second tube against each other as the lid relatively moves toward the housing.

Advantageous Effects of the Invention

According to the tube joining apparatus of the present invention, the tube holding part holds the first tube and the second tube individually in the state of being placed side by side in the oblique direction. This allows a user to set the tubes individually while visually checking the disposed positions of the tubes in the tube holding part, and suitably visually check whether the set tubes are set properly. Thus, there is no need to place the tubes on each other in setting, and it can be suitably visually checked whether the tubes are properly set in the tube holding part. Consequently, it is possible to suitably prevent occurrence of setting errors of the tubes such as twists in the tubes.

BRIEF DESCRIPTION OF DRAWINGS

FIG. 4A is a diagram before a first tube and a second tube are set, and FIG. 4B is a diagram when the first tube and the second tube are set.

FIG. 9A is a cross-sectional view taken along line 9A-9A in FIG. 4B, and FIG. 9B is a cross-sectional view taken along line 9B-9B in FIG. 4B.

DESCRIPTION OF EMBODIMENTS

Figure 1:
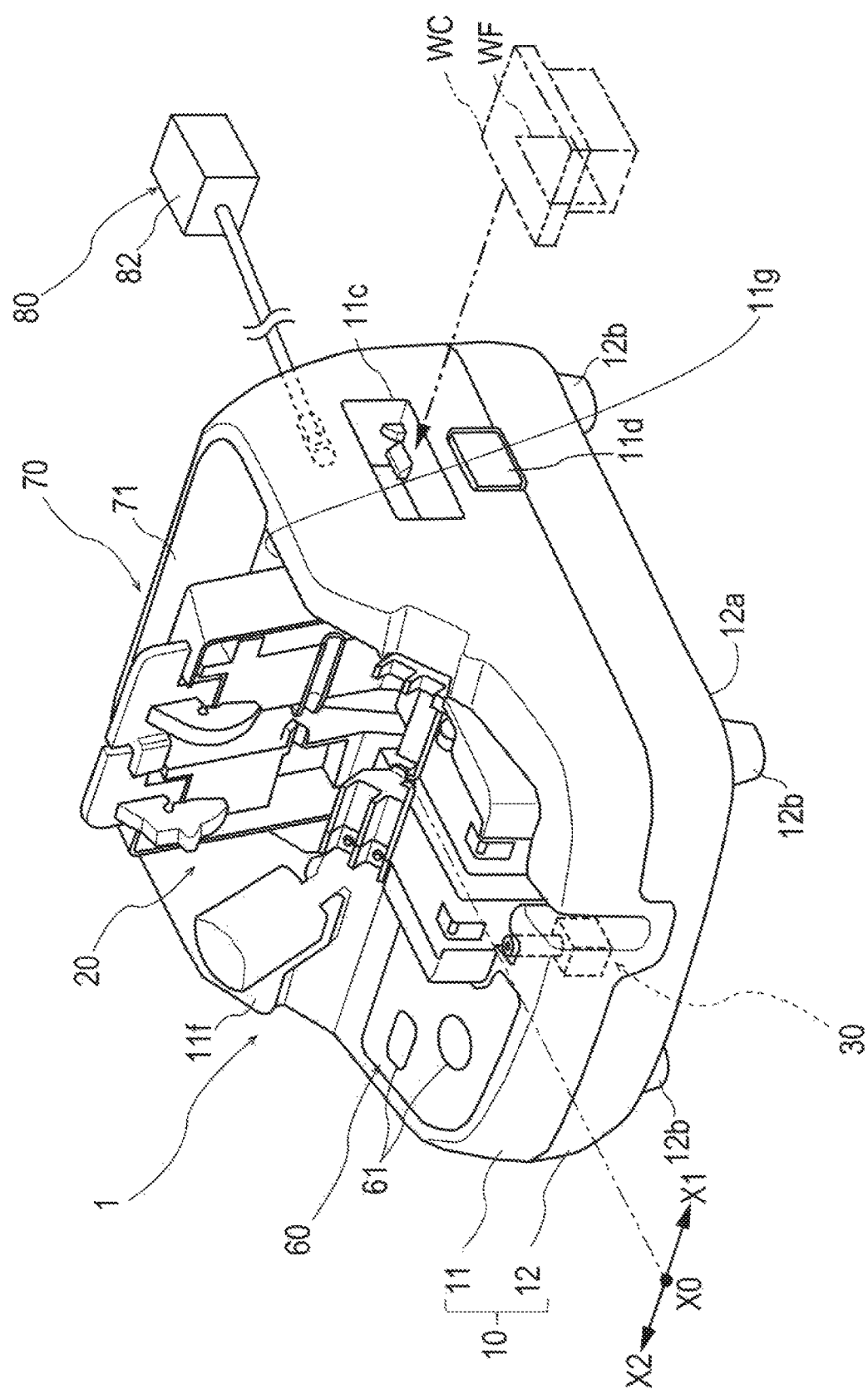
FIG. 1 is a schematic perspective view showing a tube joining apparatus with a lid open according to an embodiment of the present invention.

An embodiment of the present invention will be described below with reference to the drawings. Dimensional ratios in the drawings are exaggerated for the convenience of illustration, and may differ from actual ratios.

Figure 2:
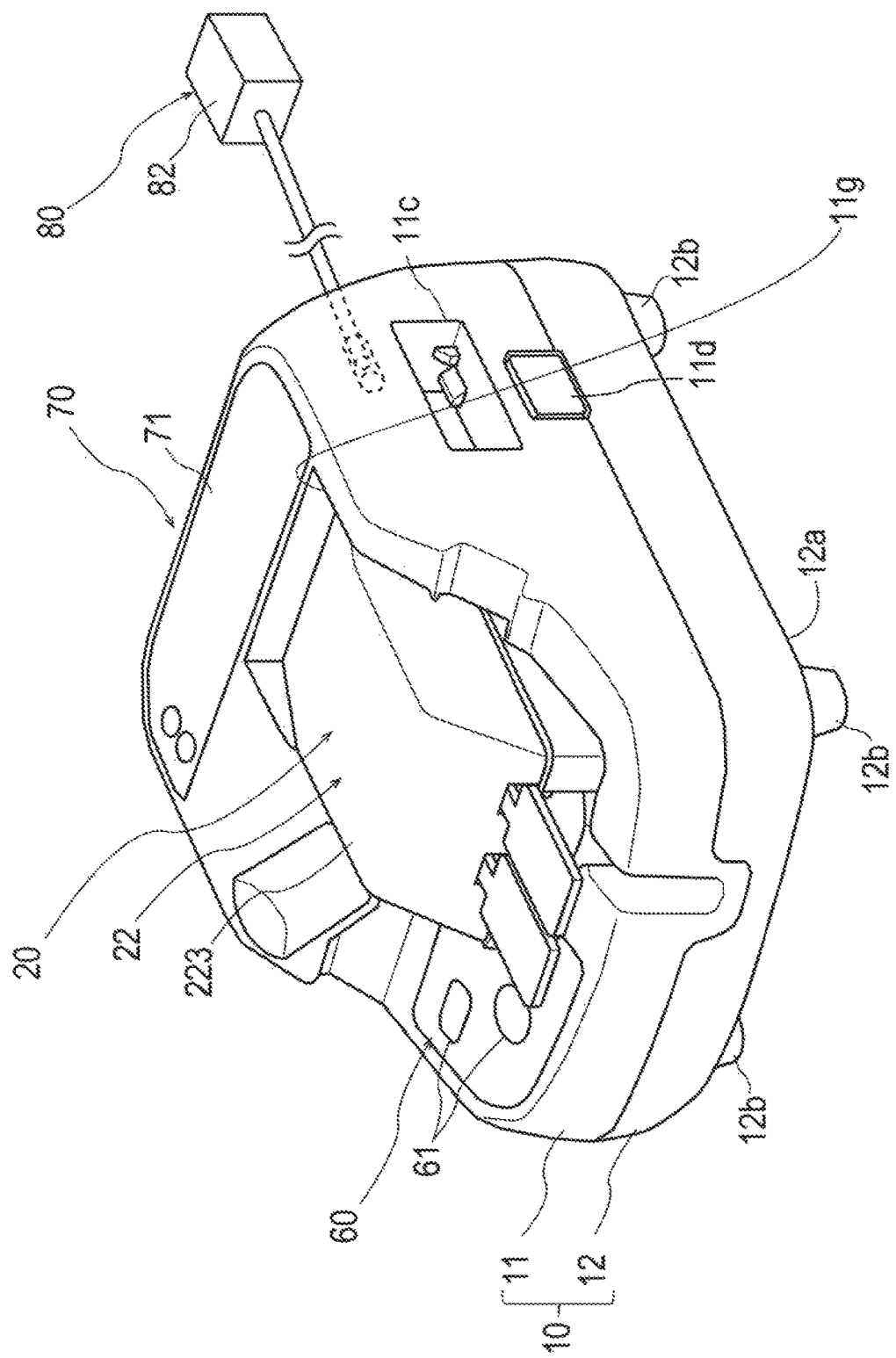
FIG. 2 is a schematic perspective view showing the tube joining apparatus with the lid closed.
Figure 3:
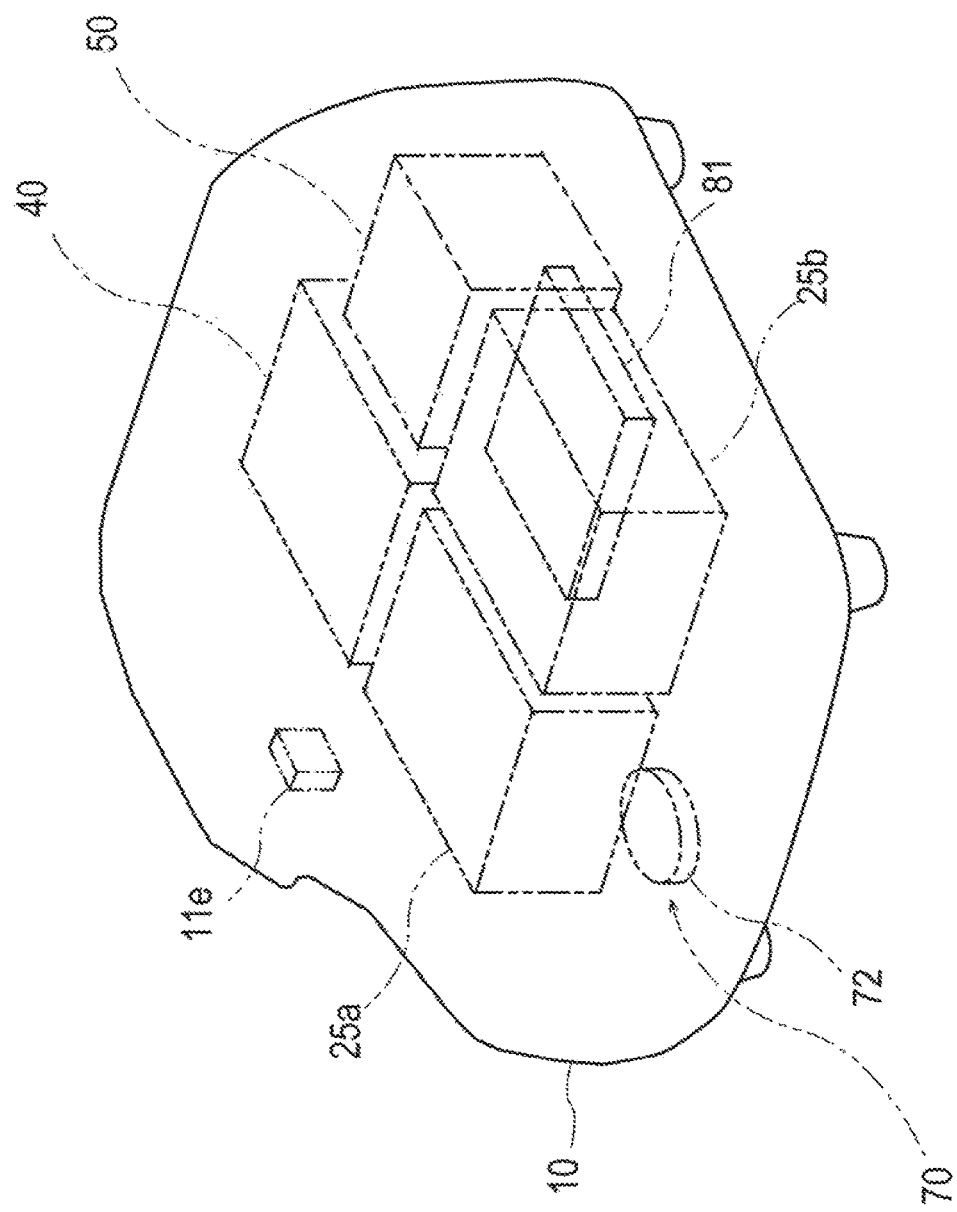
FIG. 3 is a schematic perspective view showing an arrangement example of components disposed in a housing of the tube joining apparatus when the lid is closed.
Figure 14:
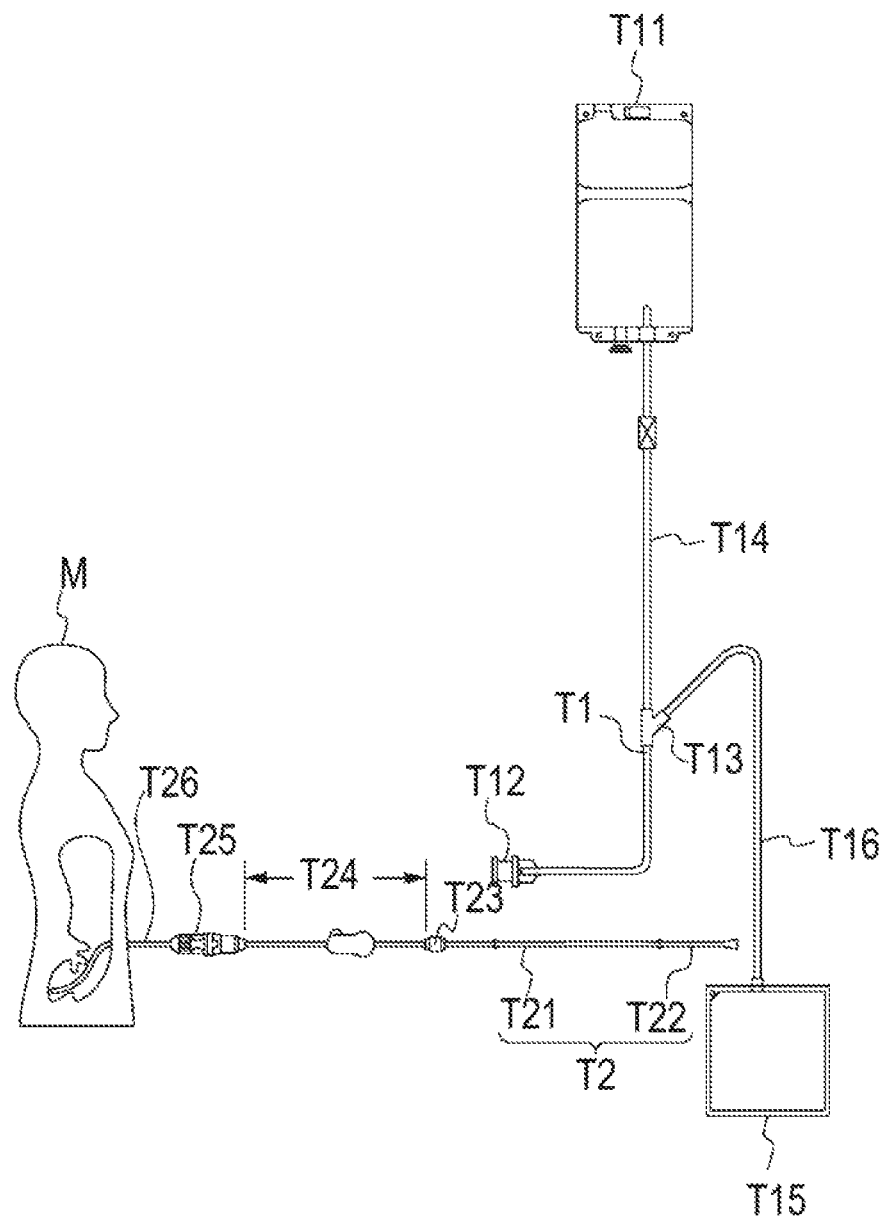
FIG. 14 is a diagram schematically showing the first tube and the second tube to be cut and joined by the tube joining apparatus.
Figure 15A:
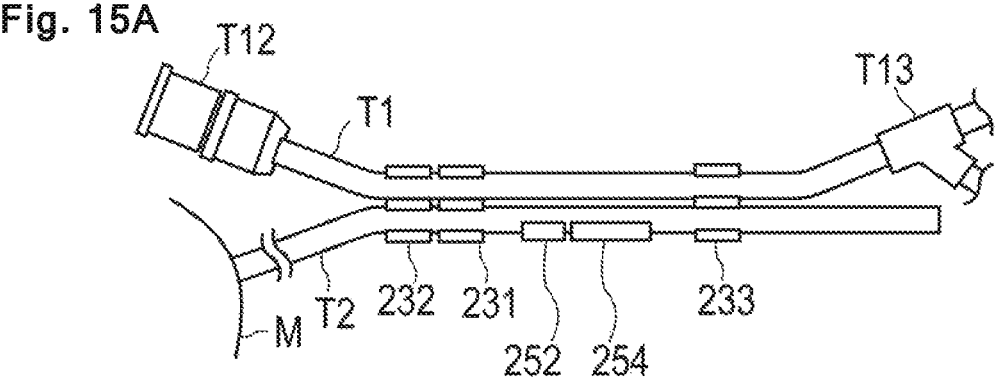
FIG. 15A, FIG. 15B, FIG. 15C and FIG. 15D are diagrams schematically showing steps of a cutting and position exchange operation by the tube joining apparatus.
Figure 15B:
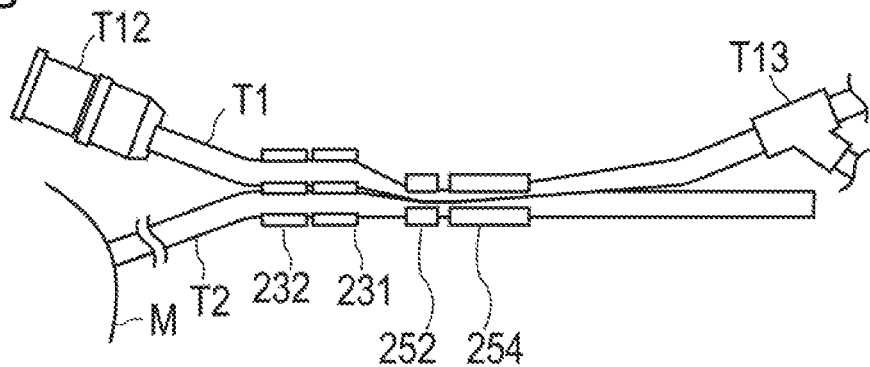
Figure 15C:
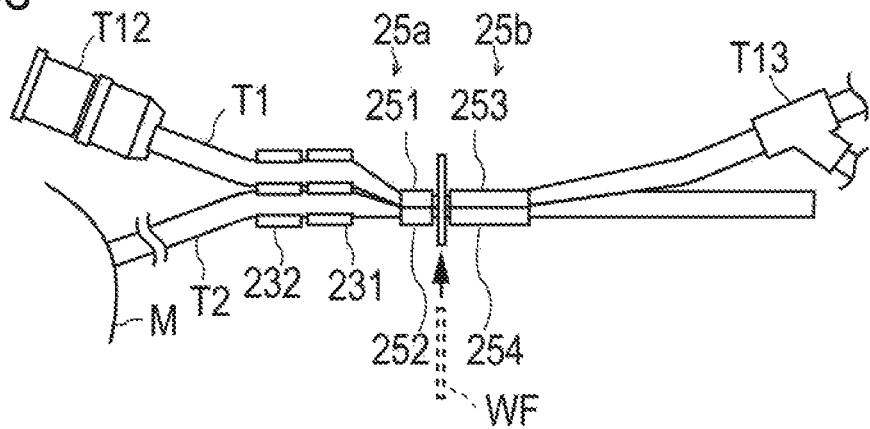
Figure 15D:
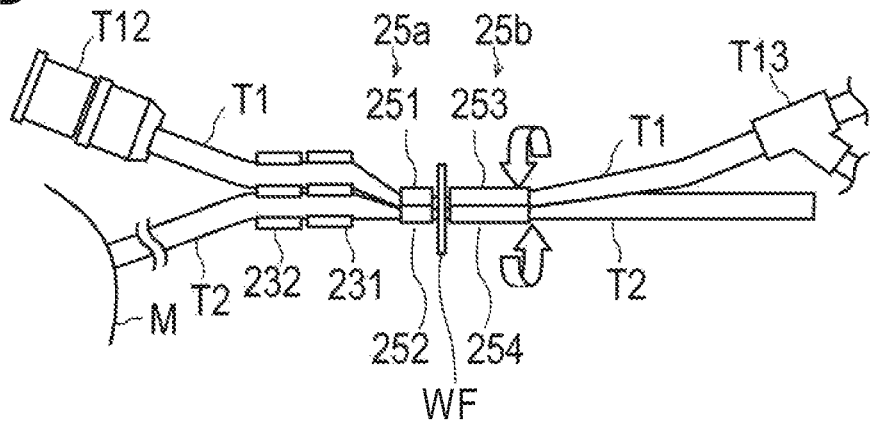
Figure 16A:
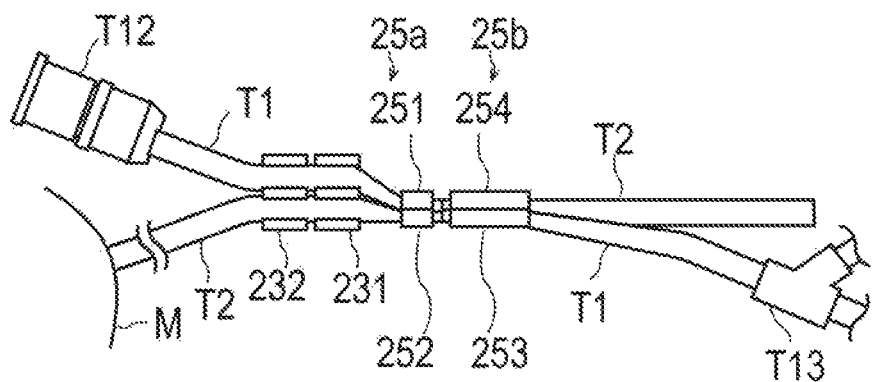
FIG. 16A, FIG. 16B, and FIG. 16C are diagrams schematically showing steps of a joining and removal operation by the tube joining apparatus.
Figure 16B:
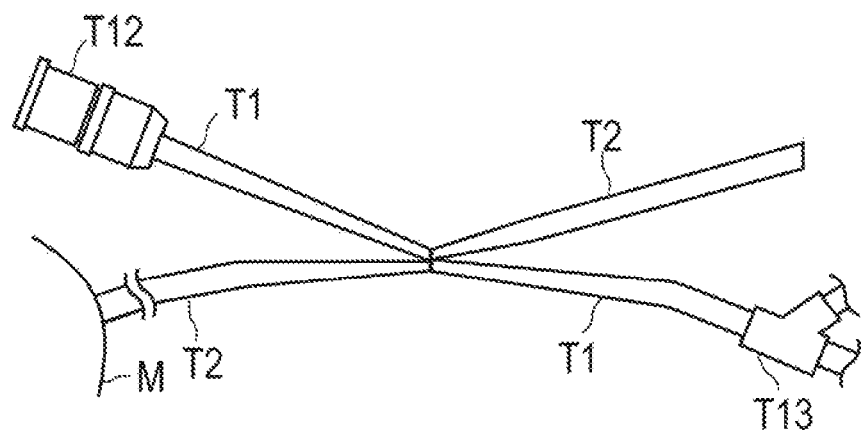
Figure 16C:
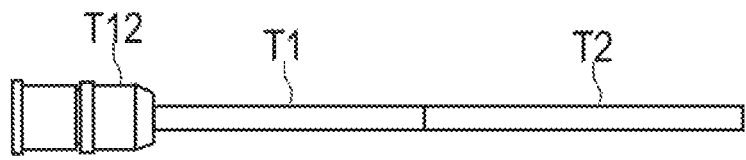
Figure 16C:
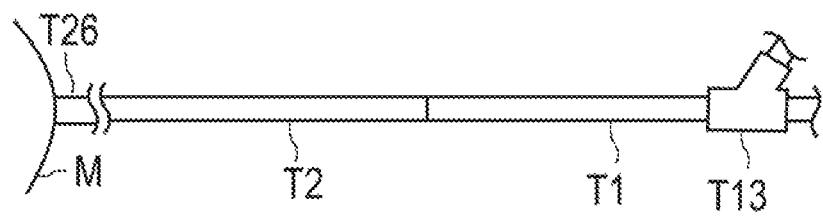

FIGS. 1 to 3 are diagrams for explaining the overall configuration of a tube joining apparatus 1 according to the present embodiment. FIGS. 4A to 13 are diagrams for explaining the configurations of parts of the tube joining apparatus 1. FIG. 14 is a diagram for explaining a first tube T1 and a second tube T2 to be joined by the tube joining apparatus 1. FIG. 15A, FIG. 15B, and FIG. 15 C and FIG. 16A, FIG. 16B, and FIG. 16C are diagrams for explaining an example of use of the tube joining apparatus 1.

As shown in FIG. 14, a tube joining set S in the present embodiment is configured as a medical apparatus that cuts by melting and joins an end portion of a tube on the side of a peritoneal dialysate bag T11 (corresponding to the "first tube T1") and an end portion of a tube on the side of a peritoneal catheter T26 of a patient (user M) used for peritoneal dialysis (corresponding to the "second tube T2").

As shown in FIG. 1, the tube joining set S includes a tube joining apparatus 1 capable of cutting by melting and joining the first tube T1 and the second tube T2, and a wafer cassette WC including a plurality of wafers WF (corresponding to "plate-shaped cutting members" used for cutting by melting. The wafer cassette WC is inserted into the tube joining apparatus 1. As shown in FIGS. 15A to 15C, the first tube T1 and the second tube T2 placed side by side are pressed against each other to be flattened, and cut by melting by a heated wafer WF. Thereafter, as shown in FIGS. 15D and 16A, the positions of one side of the first tube T1 and one side of the second tube T2 cut are exchanged, and pressurized to be joined. Hereinafter, the configurations of parts of the tube joining set S will be described.

<Tube Joining Apparatus>

An overview of the tube joining apparatus 1 will be provided. As shown in FIG. 1, the tube joining apparatus 1 includes a housing 10 that houses parts of the tube joining apparatus 1, a clamp 20 that sandwiches and presses the first tube T1 and the second tube T2 against each other and flattens them for cutting by melting, and exchanges the positions of one side of the first tube and one side of the second tube after cutting, and an interlock 30 that locks the clamp 20 in a state of sandwiching the first tube T1 and the second tube T2 during cutting and joining. Further, as shown in FIG. 3, the tube joining apparatus 1 includes a wafer cassette storage unit 40 that stores the wafer cassette WC inserted into the housing 10, and a wafer feed unit 50 that heats and feeds a wafer WF to a cutting position. Further-more, as shown in FIG. 1, the tube joining apparatus 1 includes an operation unit 60 that can accept a cutting and joining instruction etc. from the user M, a notification unit 70 that notifies the user M of necessary information, a power supply 80 capable of supplying power to the parts, and a controller 90 that performs centralized control of the operations of the parts.

Figure 4A:
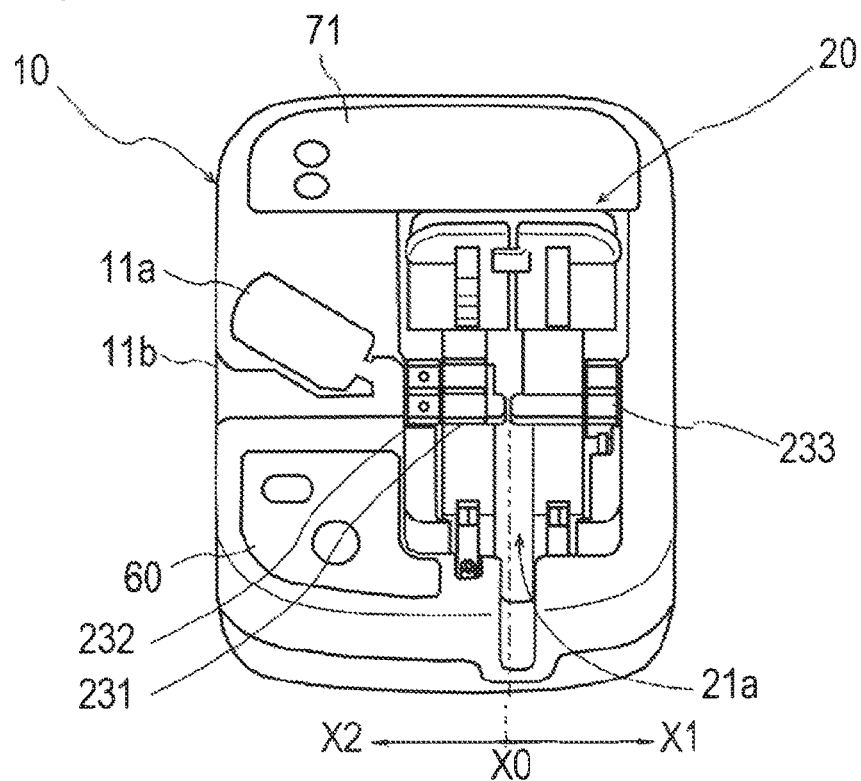
FIG. 4A and FIG. 4B are schematic plan vices views of the tube joining apparatus with the lid open.
Figure 4B:
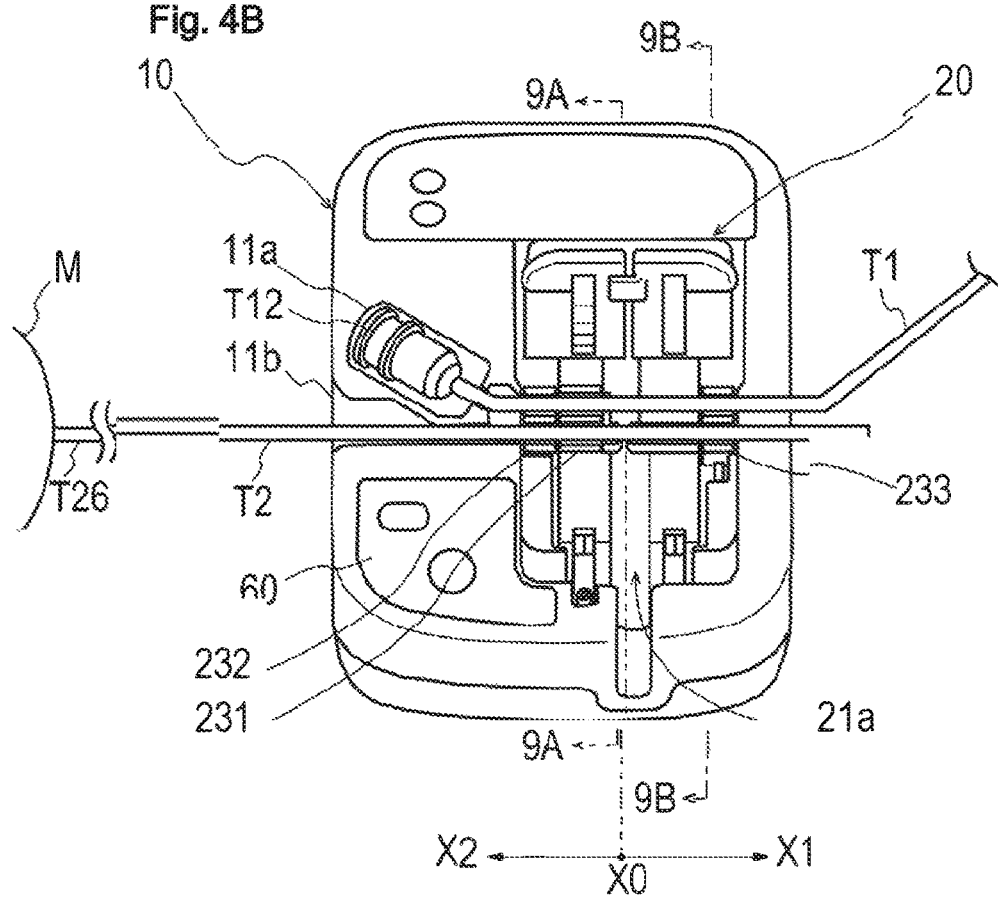

As shown in FIGS. 1, 4A and 4B, with a cutting position X0 of the tubes T1 and T2 as a boundary in an extending direction of the tubes T1 and T2, the side on which the positions of the tubes T1 and T2 are exchanged after cutting is referred to as an "exchanged side X1", and the opposite side as a "fixed side X2". Hereinafter, the configurations of the parts of the tube joining apparatus 1 will be described in detail.

(Housing)

The housing 10 has a function of housing the parts of the tube joining apparatus 1.

As shown in FIG. 1, the housing 10 is formed by a case that is the combination of an upper part 11 having a substantially prismoid-shaped outer shape and a lower part 12 having a substantially quadrangular prism-shaped outer shape disposed below the upper part 11. Hereinafter, the configurations of the parts of the housing 10 will be described.

The operation unit 60 is provided on the front side of a top surface of the upper part 11. A display 71 of the notification unit 70 described later is provided on the back side of the top surface of the upper part 11.

The upper part 11 has an inclined surface 11f inclined toward a bottom surface 12a of the lower part 12 from the back side toward the front side between the operation unit 60 and the display 71. As shown in FIG. 4A and FIG. 4B, the inclined surface 11f is provided with a recess 11a into which a predetermined connector T12 connected to the first tube T1 can be fitted, and a recess 11b into which the fixed side X2 of the second tube T2 can be fitted. This allows the user to set the first tube T1 and the second tube T2 in proper positions without mistaking the disposed positions of the tubes T1 and T2.

As shown in FIG. 1, a hole 11g in which the clamp 20 can be fitted is provided in the top surface of the upper part 11.

In a side surface of the upper part 11, a cassette insertion hole 11c for inserting the wafer cassette WC and an ejection switch 11d for ejecting the wafer cassette WC inserted in the housing 10 are provided. If the user M pushes the ejection switch 11d with a finger when the wafer cassette WC has been inserted through the cassette insertion hole 11c, the wafer cassette WC can be ejected from the housing 10 through the cassette insertion hole 11c.

As shown in FIG. 3, a temperature sensor 11e capable of measuring the ambient temperature around the housing 10 is contained in the upper part 11. Heating time during which a wafer WF heats the first tube T1 and the second tube T2 can be adjusted, according to the ambient temperature measured by the temperature sensor 11e.

As shown in FIG. 1, the lower part 12 includes the flat bottom surface 12a and four legs 12b that are provided at the four corners of the bottom surface 12a and in contact with a placement place such as a table. The bottom surface 12a is provided with a plurality of through holes for facilitating the propagation of the sound of a speaker 72 of the notification unit 70 described later to the outside of the housing 10, a plurality of through holes for discharging heat and gas generated when the first tube T1 and the second tube T2 are cut by melting to the outside of the housing 10, etc. (not shown).

Figure 9A:
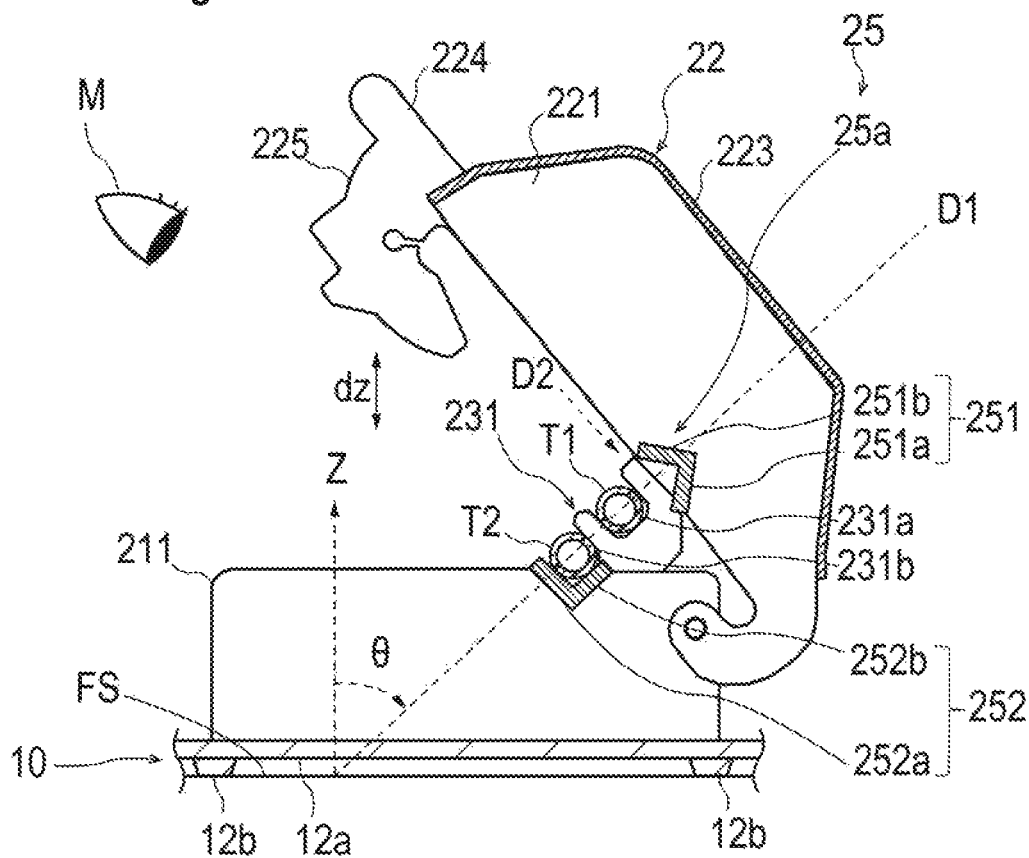
FIGS. 9A and 9B are diagrams showing the tube joining apparatus with the lid open.

In the description, when it is assumed that the housing 10 is placed on a flat placement surface FS (e.g., a table) as shown in FIG. 9A, a direction perpendicular to the placement surface FS is referred to as a "height direction Z" of the housing 10. In the present embodiment, the height direction Z is also a direction dz in which a lid 22 relatively moves toward or away from the housing 10. In actual use, the housing 10 does not necessarily have to be placed on the flat placement surface FS.

(Clamp)

The clamp 20 has a function of holding the first tube T1 and the second tube T2 in a state of being placed side by side, a function of pressing the first tube T1 and the second tube T2 against each other to flatten them for cutting, and a function of exchanging the positions of one side of the first tube T1 and one side of the second tube T2 after cutting.

Figure 5:
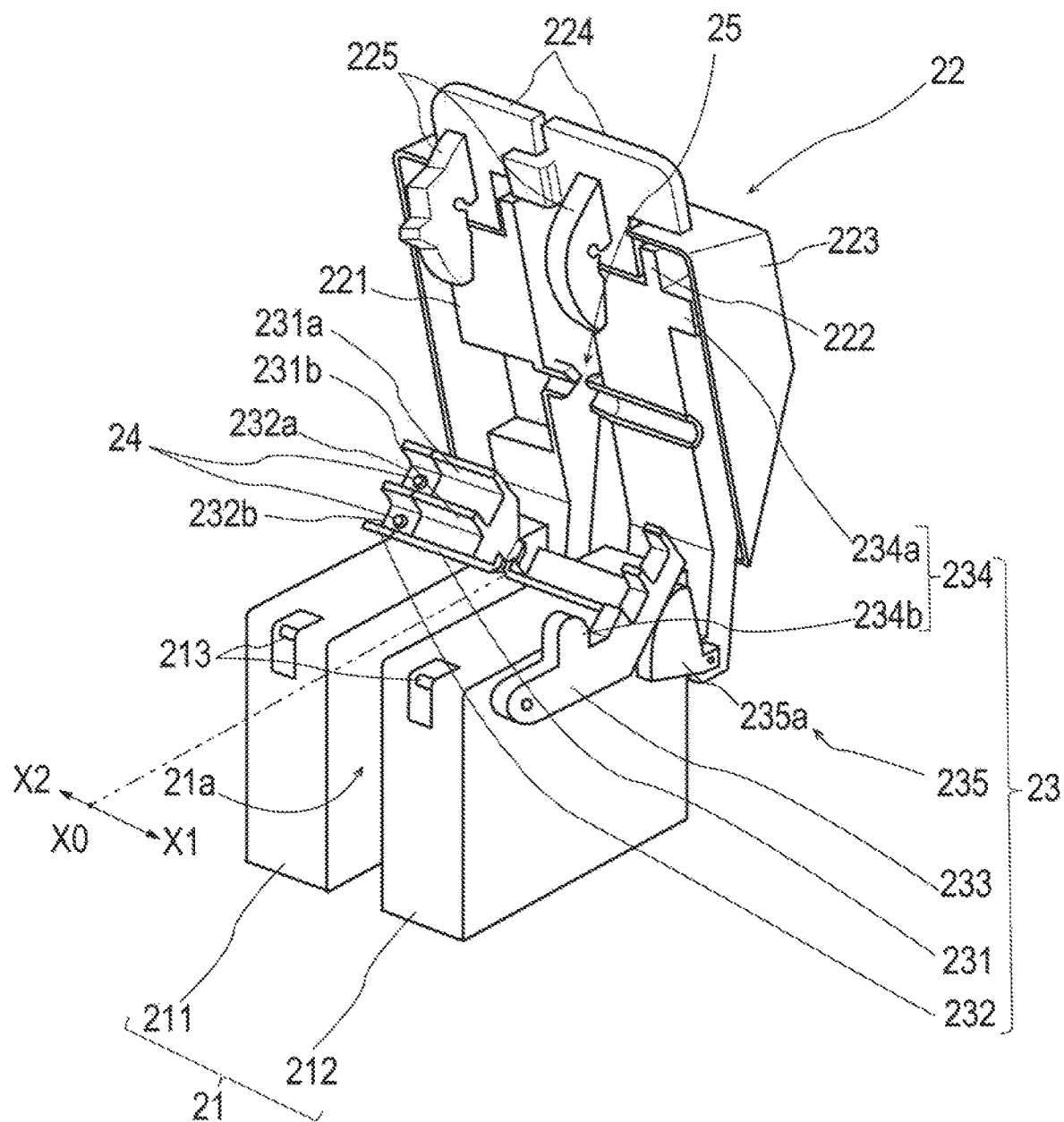
FIG. 5 is an enlarged schematic perspective view n

As shown in FIG. 5, the clamp 20 includes a pedestal 21 fixed to the bottom surface 12a of the housing 10, the lid 22 configured to be openable and closable by relatively moving toward and away from the pedestal 21, a tube holding part 23 provided on the pedestal 21 for holding the first tube T1 and the second tube T2, tube detection sensors 24 capable of detecting whether the first tube T1 and the second tube T2 are set, and a tube pressing part 25 that presses the first tube T1 and the second tube T2 against each other to flatten them as the lid 22 relatively moves toward the pedestal 13. Hereinafter, the configurations of the parts of the clamp 20 will be described.

First, the pedestal 21 will be described.

The pedestal 21 includes a first pedestal 211 provided on the fixed side X2 of the first tube T1 and the second tube T2, and a second pedestal 212 provided on the exchanged side X1 of the first tube T1 and the second tube T2. A space 21a is provided between the first pedestal 211 and the second pedestal 212 along the extending direction of the first tube T1 and the second tube T2. The space 21a is a space through which a wafer WF passes when the wafer WF before use moves to the cutting position and when the wafer WF after use is sent out of the housing 10.

The first pedestal 211 and the second pedestal 212 are each provided with an engaged part 213 on which an engaging claw 225 of the lid 22 described later is hooked to be fixed.

Next, the lid 22 will be described.

The lid 22 includes a first clamp arm 221 provided rotatably with respect to the first pedestal 211, a second clamp arm 222 provided rotatably with respect to the second pedestal 212, a cover 223 covering the first clamp arm 221 and the second clamp arm 222, and grips 224 that are provided rotatably with respect to the clamp arms 221 and 222 and can be held by the user M.

The clamp arms 221 and 222 are configured to be individually rotatable.

The cover 223 integrally covers the first clamp arm 221 and the second clamp arm 222. Thus, as shown in FIG. 2, when the lid 22 is closed, the cover 223 covers the first pedestal 211, the second pedestal 212, and an area therebetween where cutting and joining is performed.

As shown in FIG. 5, the grips 224 have the engaging claws 225 engageable with the engaged parts 213 of the pedestal 21. Thus, as shown in FIGS. 11 and 12, by rotating the grips 224 with respect to the clamp arms 221 and 222 after the clamp arms 221 and 222 and the cover 223 are closed, the engaging claws 225 are engaged with the engaged parts 213 of the pedestal 21. This can suitably keep the clamp 20 sandwiching the tubes T1 and T2.

Next, the tube holding part 23 will be described.

As shown in FIG. 5, the tube holding part 23 includes a first holding part 231 and a second holding part 232 that immovably hold the fixed sides X2 of the tubes T1 and T2, a third holding part 233 that movably holds the exchanged sides X1 of the tubes T1 and T2, a release part 234 that can switch the third holding part 233 from a holding state of holding the tubes T1 and T2 to a release state of releasing the holding, and a restoration part 235 that can switch the third holding part 233 from the release state to the holding state. Hereinafter, the configurations of the parts of the tube holding part 23 will be described.

First, the first holding part 231, the second holding part 232, and the third holding part 233 will be described.

The first holding part 231 is fixed to a top surface of the first pedestal 211. The first holding part 231 includes a recessed first groove 231a into which the first tube T1 can be fitted, and a recessed second groove 231b into which the second tube T2 can be fitted.

As shown in FIG. 9A, the first groove 231a and the second groove 231b are provided in a line in a direction tilted at an angle θ with respect to the height direction Z of the housing 10 (oblique direction D1). Thus, the first tube T1 and the second tube T2 are held in the first holding part 231, placed side by side in the oblique direction D1. The first groove 231a disposed on the back side in the direction D1 in which the first tube T1 and the second tube T2 are placed side by side is disposed in a position higher than that of the second groove 231b in the height direction Z of the housing 10.

The grooves 231a and 231b are recessed on the top surface side of the first holding part 231 along a direction D2 orthogonal to the oblique direction D1. Thus, the tubes T1 and T2 are set by being inserted from the direction D2 orthogonal to the direction D1 in which they are placed side by side. This allows the user M to easily insert and set the tubes T1 and T2 when the lid 22 is open.

As shown in FIG. 5, the second holding part 232 is fixed to a side surface of the first pedestal 211, adjacent to the first holding part 231. Like the first holding part 231, the second holding part 232 includes a recessed third groove 232a into which the first tube T1 can be fitted, and a recessed fourth groove 232b into which the second tube T2 can be fitted. Like the first groove 231a and the second groove 231b of the first holding part 231, the third groove 232a and the fourth groove 232b are provided in a line in the oblique direction D1.

Figure 9B:
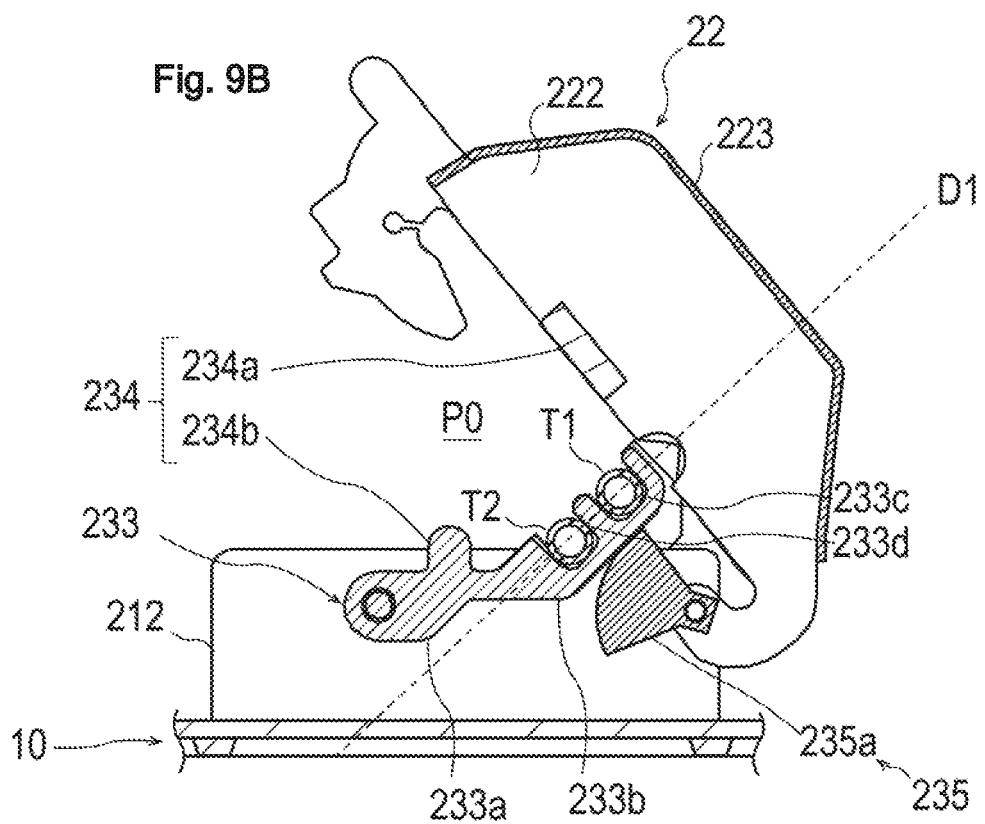

As shown in FIG. 9B, the third holding part 233 includes a base 233a rotatably provided at a side surface of the second pedestal 212, and a bent portion 233b bent from and continuous with the base 233a.

The bent portion 233b is provided with a recessed fifth groove 233c into which the exchanged side X1 of the first tube T1 can be fitted, and a recessed sixth groove 233d into which the exchanged side X1 of the second tube T2 can be fitted.

Figure 12A:
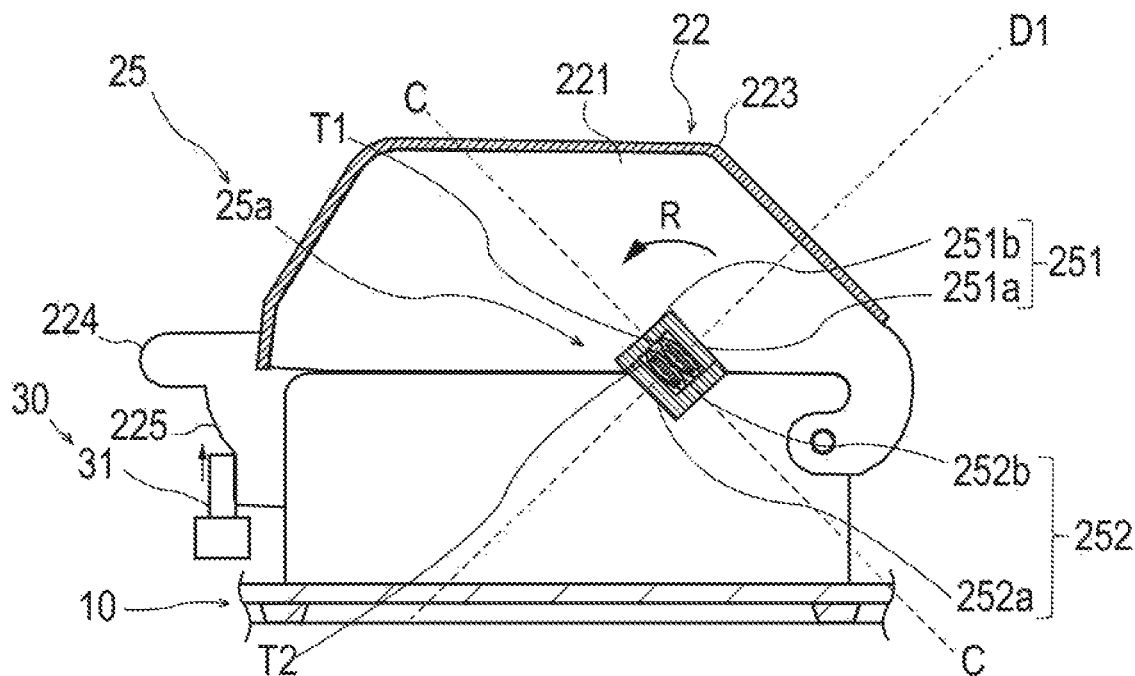
FIG. 12A and FIG. 12B are diagrams showing the tube joining apparatus with the lid closed.
Figure 12B:
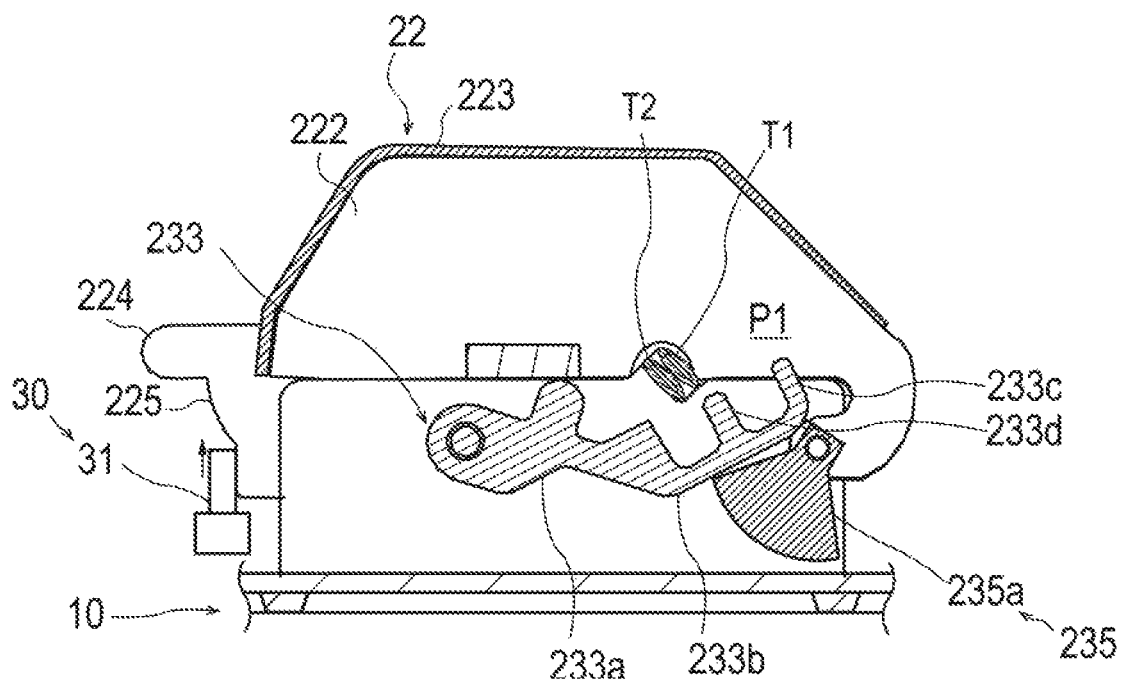

The third holding part 233 is configured to be movable between a position shown in FIG. 9B in which the fifth groove 233c and the sixth groove 233d are in a line along the oblique direction D1, and the third holding part 233 can hold the tubes T1 and T2 with the first holding part 231 and the second holding part 232 (referred to as a "holding position P0"), and a position shown in FIG. 12B in which the third holding part 233 has released holding (referred to as a "release position P1").

In the present embodiment, as shown in FIG. 9A, the angle θ formed between the oblique direction D1 and the height direction Z of the housing 10 is 45 degrees. That is, the holding parts 231, 232, and 233 hold the first tube T1 and the second tube T2 such that an imaginary line (indicated by a chain line in the figure) connecting the axis of the first tube T1 and the axis of the second tube T2 forms an angle of 45 degrees with respect to the height direction Z. However, the angle θ is not limited to a particular angle as long as it is larger than 0 degrees and smaller than 90 degrees.

Thus, the holding parts 231, 232, and 233 hold the tubes T1 and T2 individually in a state of being placed side by side in the oblique direction D1 with respect to the height direction Z of the housing 10. As shown in FIG. 9A, the user M sits on a chair or the like and uses the tube joining apparatus 1 placed on a table or the like, looking into it from obliquely above. Thus, the user M can set the tubes T1 and T2 in the holding parts 231, 232, and 233 without changing his or her posture. Further, the user M can easily visually check whether the set tubes T1 and T2 are properly set (the presence or absence of a twist or the like).

For example, when the angle θ=0 degrees (when the first tube T1 and the second tube T2 are placed side by side in the height direction Z), the grooves 231b, 232b, and 233d and the second tube T2 disposed on the lower side (the pedestal 21 side) are hidden behind the grooves 231a, 232a, and 233c and the first tube T1 disposed on the upper side (the lid 22 side) and difficult to check visually, since the eyes of the user M are located obliquely above the tube joining apparatus 1. Thus, the user M needs to take the trouble to stoop down to look into the tube joining apparatus 1 to check whether the tubes T1 and T2 are properly set.

For example, when the angle θ=90 degrees (when the first tube T1 and the second tube T2 are placed side by side in a horizontal direction), the grooves 231a, 232a, and 233c and the first tube T1 disposed on the back side are hidden behind the grooves 231b, 232b, and 233d and the second tube T2 disposed on the front side and difficult to check visually, since the eyes of the user M are located obliquely above the tube joining apparatus 1. Thus, the user M needs to take the trouble to bend forward to the back side to look into the tube joining apparatus 1 to check whether the tubes T1 and T2 are properly set.

In terms of visually checking whether the tubes T1 and T2 are properly set, the angle θ is preferably 30 degrees or more and less than 90 degrees, for example.

Next, the release part 234 and the restoration part 235 will be described.

As shown in FIG. 5, the release part 234 includes a flat surface 234a continuous with a side surface of the second clamp arm 222, and a protrusion 234b protruding from the base 233a of the third holding part 233 toward the flat surface 234a of the second clamp arm 222.

Figure 10A:
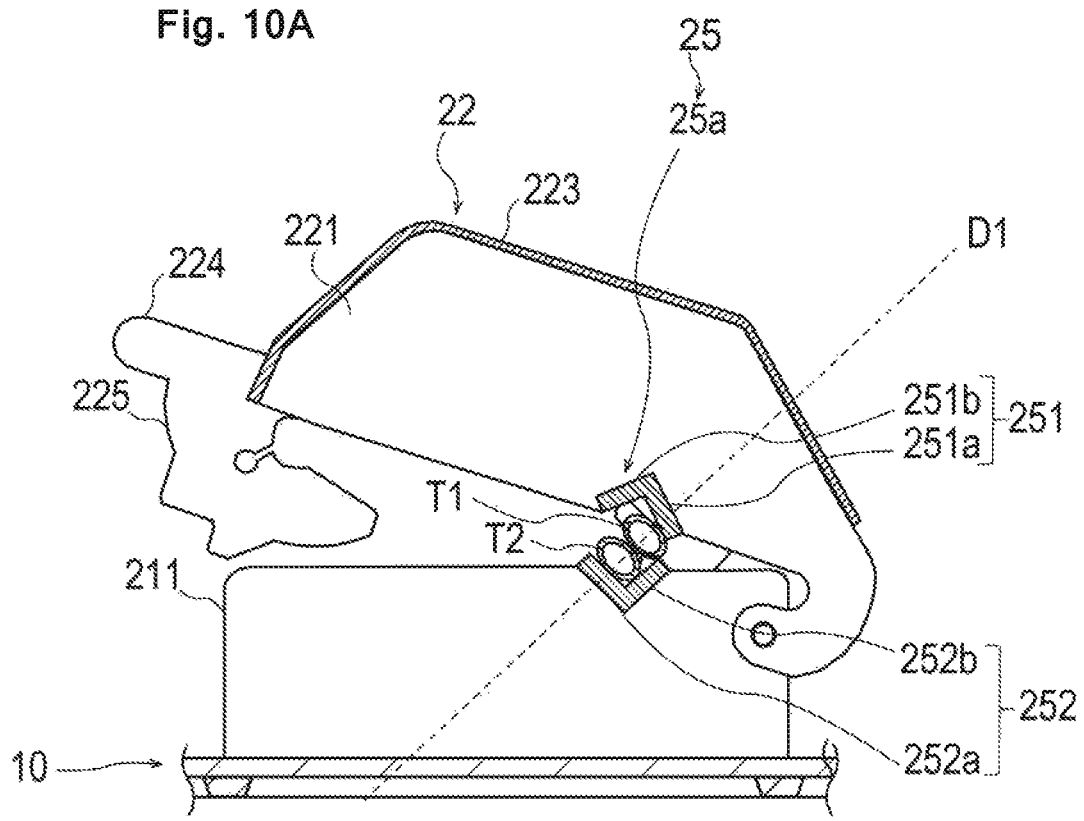
FIGS. 10A and 10B are diagrams showing the tube joining apparatus when the lid is being moved toward the housing.
Figure 11A:
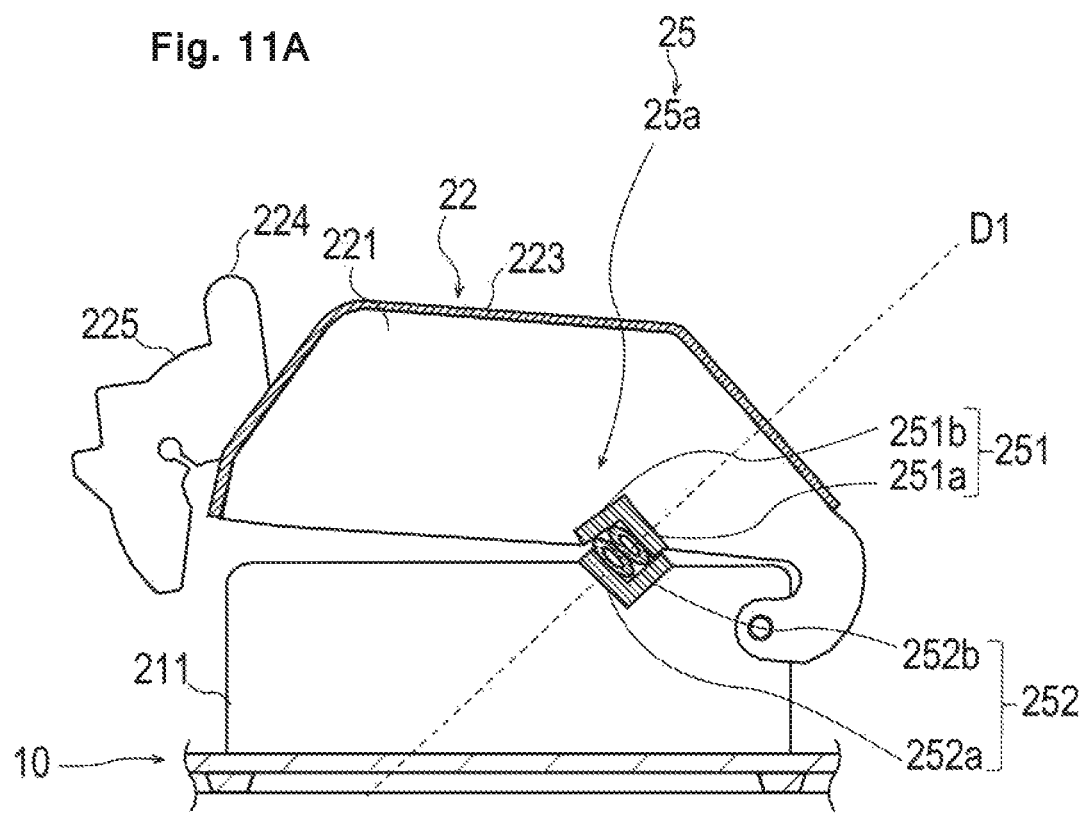
FIGS. 11A and 11B are diagrams showing the tube joining apparatus when the lid is being moved toward the housing.
Figure 11B:
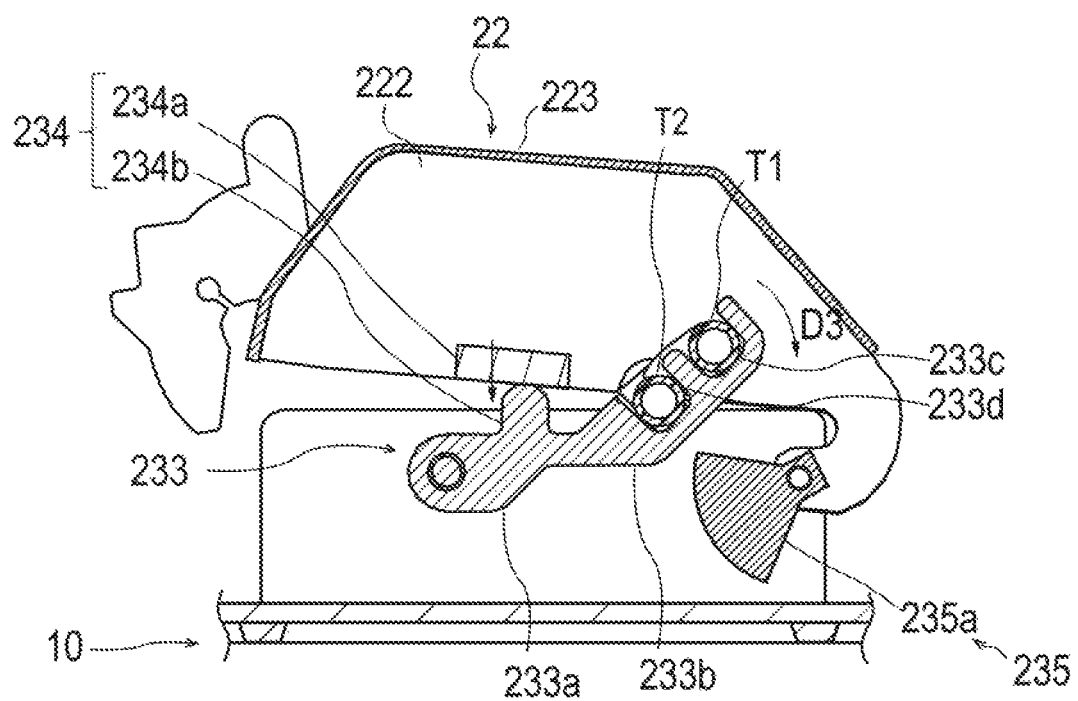

As shown in FIG. 11B, the protrusion 234b provided at the third holding part 233 comes into contact with the flat surface 234a provided at the lid 22 as the lid 22 relatively moves toward the housing 10. In the present embodiment, after the tube pressing part 25 described later sandwiches the first tube T1 and the second tube T2 (see FIG. 10A), and before the lid 22 is completely closed (see FIG. 12B), the protrusion 234b comes into contact with the flat surface 234a. When the lid 22 is further pushed down (relatively moved toward the housing 10) from the state of FIG. 11B in which the protrusion 234b is in contact with the flat surface 234a, the third holding part 233 is pushed down in a direction D3 to move away from the lid 22, releasing the holding of the tubes T1 and T2. Thus, the release part 234 is configured to retract the third holding part 233 from the holding position P0 to the release position P1 as the lid 22 relatively moves toward the housing 10.

As shown in FIG. 9B, the restoration part 235 includes a cam 235a that can push up the third holding part 233 in conjunction with the relative movement of the second clamp arm 222 of the lid 22 away from the housing 10.

Figure 10B:
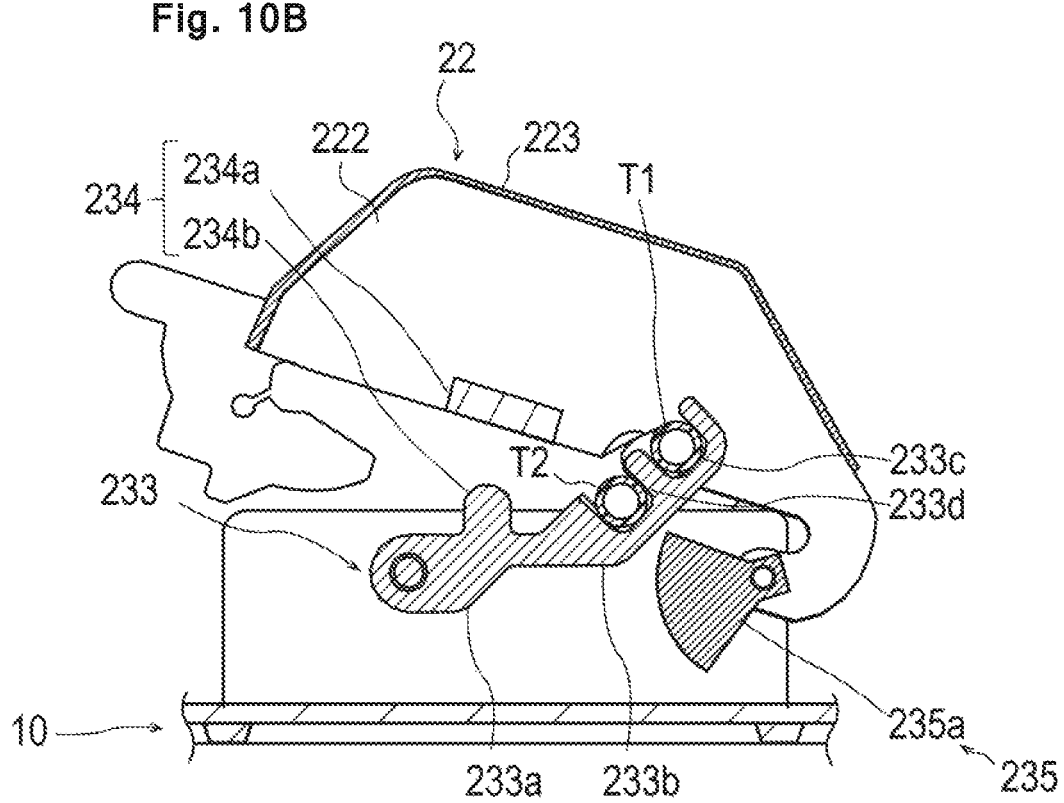

The cam 235a has a substantially fan-shaped outer shape in an arrow view from the direction of the side of the housing 10. The cam 235a is fixed near a rotating portion of the second clamp arm 222. Thus, the cam 235a also rotates in conjunction with the rotation of the second clamp arm 222. When the lid 22 is opened to some degree, a curved surface of the cam 235a is in contact with a bottom surface of the third holding part 233, keeping the third holding part 233 in the holding position P0. As shown in FIG. 10B, when the lid 22 is relatively moved toward the housing 10, the curved surface of the cam 235a moves away from the third holding part 233 before the protrusion 234b of the release part 234 comes into contact with the flat surface 234a. Thus, when the lid 22 is moved from an open position to a closed position, the cam 235a does not prevent the third holding part 233 from being moved from the holding position P0 to the release position P1 by the release part 234. On the other hand, when the lid 22 is moved from the closed position to the open position, the cam 235a comes into contact with the third holding part 233 to push up the third holding part 233. As a result, the third holding part 233 is returned from the release position P1 to the holding position P0.

As described above, the third holding part 233 is configured to be movable between the holding position P0 and the release position P1 by the release part 234 and the restoration part 235. Thus, the third holding part 233 does not interfere with a position exchange operation for exchanging the positions of one side of the first tube T1 and one side of the second tube T2 after cutting performed with the lid 22 closed. Further, there is no need to rotate the third holding part 233 in conjunction with a movable-side pressing part 25b that performs the position exchange operation described later, and thus the tube joining apparatus 1 can have a relatively simple structure. Furthermore, in the present embodiment, the release part 234 retracts the third holding part 233 from the holding position P0 to the release position P1 after the tube pressing part 25 described later sandwiches the first tube T1 and the second tube T2. Thus, the tube pressing part 25 can sandwich the first tube T1 and the second tube T2 with the exchanged sides X1 of the first tube T1 and the second tube T2 held in proper positions by the third holding part 233.

Next, the tube detection sensors 24 will be described.

Figure 6A:
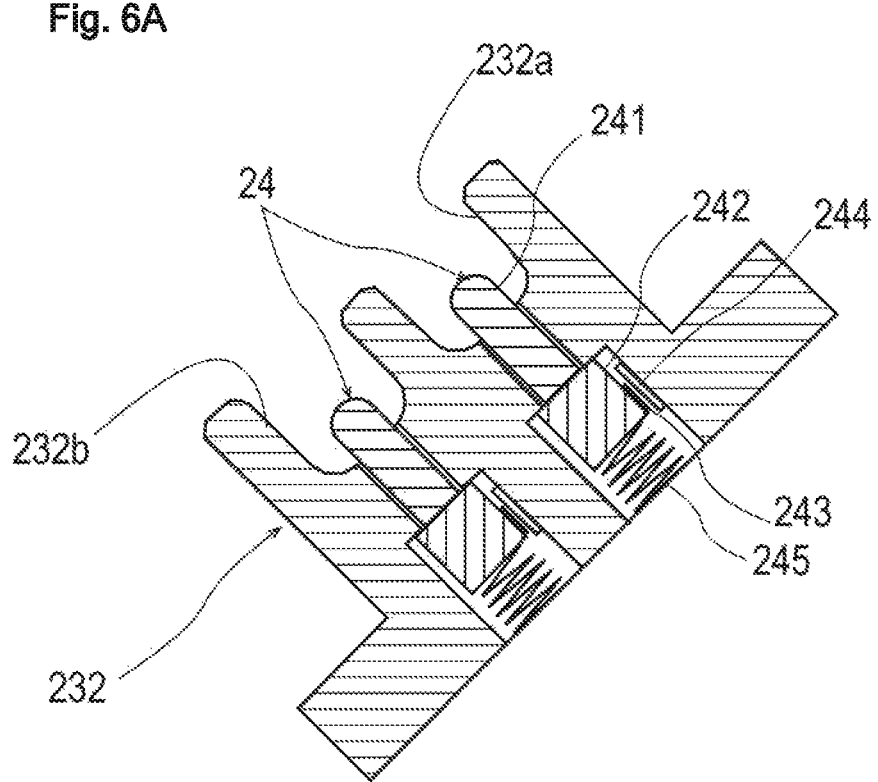
FIG. 6A and FIG. 6B are diagrams for explaining tube detection sensors provided at the clamp.
Figure 6B:
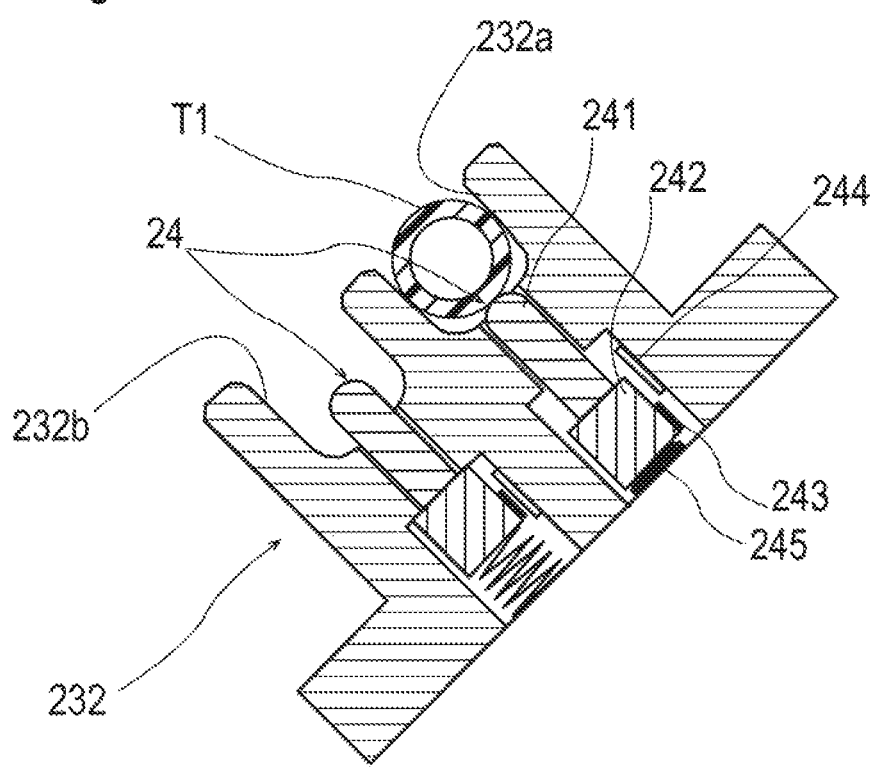

As shown in FIG. 6A and FIG. 6B, the tube detection sensors 24 are provided in the third groove 232a and the fourth groove 232b of the second holding part 232. The tube detection sensors 24 have a function of detecting whether the tubes T1 and T2 are set in the grooves 232a and 232b of the second holding part 232. Hereinafter, the configuration of the tube detection sensors 24 will be described, using the tube detection sensor 24 set in the third groove 232a as an example.

The tube detection sensor 24 includes a pin 241 that can protrude from a hole provided in the third groove 232a, a base 242 that supports the pin 241, a magnet 243 attached to the base 242, a Hall element 244 that can detect the magnetic force of the magnet 243, and a biasing member 245 that applies a biasing force to the pin 241 in a direction to protrude from the hole. In the present embodiment, the biasing member 245 is formed by a spring. However, the biasing member 245 is not limited to a particular configuration as long as it can apply a biasing force to the pin 241 in a direction to protrude from the hole.

As shown in FIG. 6A, in a state where the first tube T1 is not set in the third groove 232a, the base 242 is in contact with an inner surface of the second holding part 232, restricting the movement of the pin 241 while the pin 241 receives the biasing force of the biasing member 245. Thus, the distal end side of the pin 241 is protruded from the hole. In this state, the magnet 243 is disposed in the vicinity of the Hall element 244, and thus the magnetic force of the magnet 243 that can be detected by the Hall element 244 is strong. In contrast, as shown in FIG. 6B, when the first tube T1 is disposed in the third groove 232a, the pin 241 and the base 242 are pushed by the first tube T1 into a cavity of the second holding part 232. Consequently, the magnet 243 attached to the base 242 moves away from the Hall element 244, so that the magnetic force of the magnet 243 that can be detected by the Hall element 244 becomes weak. Thus, the tube detection sensor 24 can detect whether the first tube T1 is set in the third groove 232a and whether the first tube T1 is pushed into the back of the third groove 232a, based on the strength of the magnetic force of the magnet 243 that can be detected by the Hall element 244.

The tube detection sensors 24 may be provided in the first holding part 231 or the third holding part 233.

Next, the tube pressing part 25 will be described.

Figure 7:
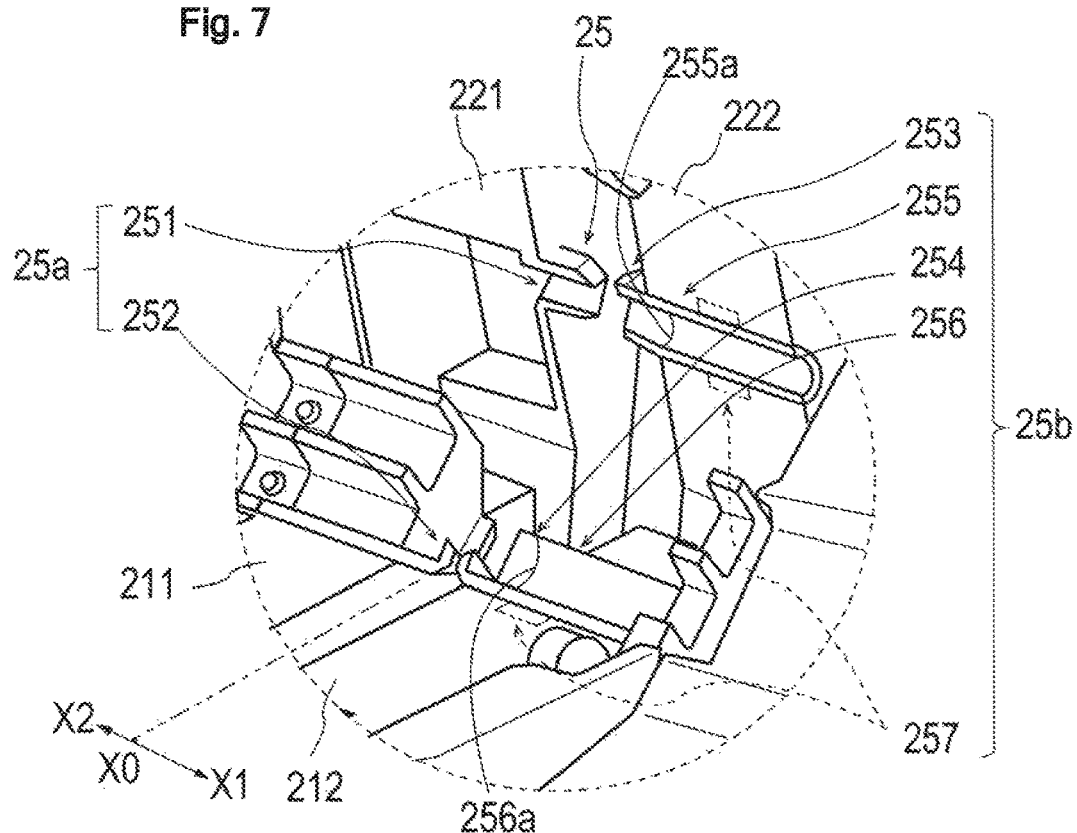
FIG. 7 is an enlarged schematic perspective view showing a tube pressing part included in the clamp.

As shown in FIG. 7, the tube pressing part 25 includes a fixed-side pressing part 25a that presses the fixed side X2 of the first tube T1 and the fixed side X2 of the second tube T2 against each other, and the movable-side pressing part 25b that presses the exchanged side X1 of the first tube T1 and the exchanged side X1 of the second tube T2 against each other, as the lid 22 relatively moves toward the housing 10. Hereinafter, the configurations of the parts of the tube pressing part 25 will be described.

First, the fixed-side pressing part 25a will be described.

The fixed-side pressing part 25a includes a lid-side pressing part 251 provided at the first clamp arm 221, and a housing-side pressing part 252 provided at the first pedestal 211. As shown in FIG. 12A, when the lid 22 is closed, the lid-side pressing part 251 and the housing-side pressing part 252 are integrated, and have a function of keeping the first tube T1 and the second tube T2 pressed against each other and flattened, and a function of holding the first tube T1 and the second tube T2 in positions during cutting and joining. Hereinafter, the configurations of the parts of the fixed-side pressing part 25a will be described.

First, the lid-side pressing part 251 will be described.

As shown in FIG. 7, the lid-side pressing part 251 is protruded from a side surface of the first clamp arm 221 toward the second clamp arm 222. As shown in FIG. 12A, the lid-side pressing part 251 includes a lid-side pressing portion 251a that applies a pressing force to the first tube T1 and the second tube T2 from the lid 22 side, and a lid-side protruding portion 251b that protrudes from the lid-side pressing portion 251a toward the housing 10, when the lid 22 is closed.

The lid-side pressing portion 251a is formed by a flat surface orthogonal to the oblique direction D1 when the lid 22 is closed. When the lid 22 is closed, the lid-side pressing portion 251a applies a pressing force to the first tube T1 in a direction to move toward the second tube T2 (a direction along the oblique direction D1).

The lid-side protruding portion 251b protrudes from the lid-side pressing portion 251a in a rotation direction R when the lid 22 is closed. Thus, as shown in FIGS. 9A to 11A, the lid-side protruding portion 251b can cover the first tube T1 and the second tube T2 to enclose them in conjunction with the relative movement of the lid 22 toward the housing 10. As shown in FIG. 12A, when the lid 22 is closed, the lid-side protruding portion 251b extends along the oblique direction D1 beyond a contact position C between the first tube T1 and the second tube T2 flattened, and is in contact with an end portion of a housing-side pressing portion 252a described later.

The surfaces of the lid-side pressing portion 251a and the lid-side protruding portion 251b on the side facing the tubes T1 and T2 (the inner surface of the lid-side pressing part 251) are of an L shape in an arrow view from the extending direction of the first tube T1 and the second tube T2.

Next, the housing-side pressing part 252 will be described.

As shown in FIG. 7, the housing-side pressing part 252 is protruded from a side surface of the first pedestal 211 toward the second pedestal 212. As shown in FIG. 12A, the housing-side pressing part 252 includes the housing-side pressing portion 252a that applies a pressing force to the first tube T1 and the second tube T2 from the housing 10 side, and a housing-side protruding portion 252b protruding from the housing-side pressing portion 252a toward the lid 22, when the lid 22 is closed.

The housing-side pressing portion 252a is formed by a flat surface orthogonal to the oblique direction D1 when the lid 22 is closed. When the lid 22 is closed, the housing-side pressing portion 252a applies a pressing force to the second tube T2 in a direction to move toward the first tube T1 (a direction along the oblique direction D1). Thus, the directions of the pressing forces applied to the tubes T1 and T2 by the housing-side pressing portion 252a and the lid-side pressing portion 251a described above coincide with the direction D1 in which the first tube T1 and the second tube T2 are placed side by side. Consequently, the housing-side pressing portion 252a and the lid-side pressing portion 251a can press the tubes T1 and T2 against each other and flatten them only by slightly moving them closer from the positions in which they are set in the tube holding part 23. Thus, when the tubes T1 and T2 are sandwiched by the clamp 20, it is not necessary to largely move the tubes T1 and T2 set by the user M, so that the user M can be given a sense of security that the displacement of the tubes T1 and T2 is unlikely to occur.

When the lid 22 is closed, the housing-side protruding portion 252b protrudes from the housing-side pressing portion 252a, opposite the above-described lid-side protruding portion 251b. When the lid 22 is closed, the housing-side protruding portion 252b extends along the oblique direction D1 beyond the contact position C between the first tube T1 and the second tube T2 flattened, and is in contact with an end portion of the lid-side pressing portion 251a. Consequently, when the lid 22 is closed, the housing-side protruding portion 252b and the lid-side protruding portion 251b are provided in positions opposite to each other, and can surround the peripheral surface of the first tube T1 and the peripheral surface of the second tube T2.

The surfaces of the housing-side pressing portion 252a and the housing-side protruding portion 252b on the side facing the tubes T1 and T2 (the inner surface of the housing-side pressing part 252) are of an L shape in an arrow view from the extending direction of the first tube T1 and the second tube T2.

Next, the operation of the fixed-side pressing part 25a will be described. As shown in FIG. 10A and FIG. 11A, when the lid 22 is relatively moved toward the housing 10, the lid-side pressing portion 251a comes into contact with the first tube T1, and the first tube T1 and the second tube T2 are sandwiched between the lid-side pressing portion 251a and the housing-side pressing portion 252a. When the lid 22 is further relatively moved toward the housing 10 from the state of FIG. 11A and the lid 22 is closed, as shown in FIG. 12A, the lid-side pressing portion 251a and the housing-side pressing portion 252a press the first tube T1 and the second tube T2 against each other along the oblique direction D1, flattening them. At this time, as the lid 22 is relatively moved toward the housing 10, the lid-side protruding portion 251b brings the first tube T1 and the second tube T2 closer to the housing-side protruding portion 252b, enclosing the first tube T1 and the second tube T2 with the housing-side protruding portion 252b. This can suitably prevent the displacement of the first tube T1 and the second tube T2 in a direction intersecting the direction D1 in which the first tube T1 and the second tube T2 are placed side by side.

Next, the movable-side pressing part 25b will be described.

As shown in FIG. 7, like the fixed-side pressing part 25a, the movable-side pressing part 25b includes a lid-side pressing part 253 protruded from a side surface of the second clamp arm 222 toward the first clamp arm 221, and a housing-side pressing part 254 protruded from a side surface of the second pedestal 212 toward the first pedestal 211. The movable-side pressing part 25b further includes a lid-side clamp member 255 continuous with the lid-side pressing part 253 and extending along the entire length of the second clamp arm 222 in the width direction, a housing-side clamp member 256 extending along the entire length of the second pedestal 212 in the width direction, and a drive unit 257 that exchanges the positions of one side of the first tube T1 and one side of the second tube T2 by rotating 180 degrees the lid-side clamp member 255 and the housing-side clamp member 256 integrated. Hereinafter, the configurations of the parts of the movable-side pressing part 25b will be described. The configuration of the lid-side pressing part 253 of the movable-side pressing part 25b is similar to the configuration of the lid-side pressing part 251 of the fixed-side pressing part 25a described above, and thus will not be described. The configuration of the housing-side pressing part 254 of the movable-side pressing part 25b is similar to the configuration of the housing-side pressing part 252 of the fixed-side pressing part 25a described above, and thus will not be described.

The lid-side clamp member 255 includes a recessed groove 255a extending along the entire length of the second clamp arm 222 in the width direction.

The housing-side clamp member 256 includes a recessed groove 256a extending along the entire length of the second pedestal 212 in the width direction. When the lid 22 is closed, the first tube T1 and the second tube T2 are sandwiched between the grooves 255a and 256a.

Figure 8:
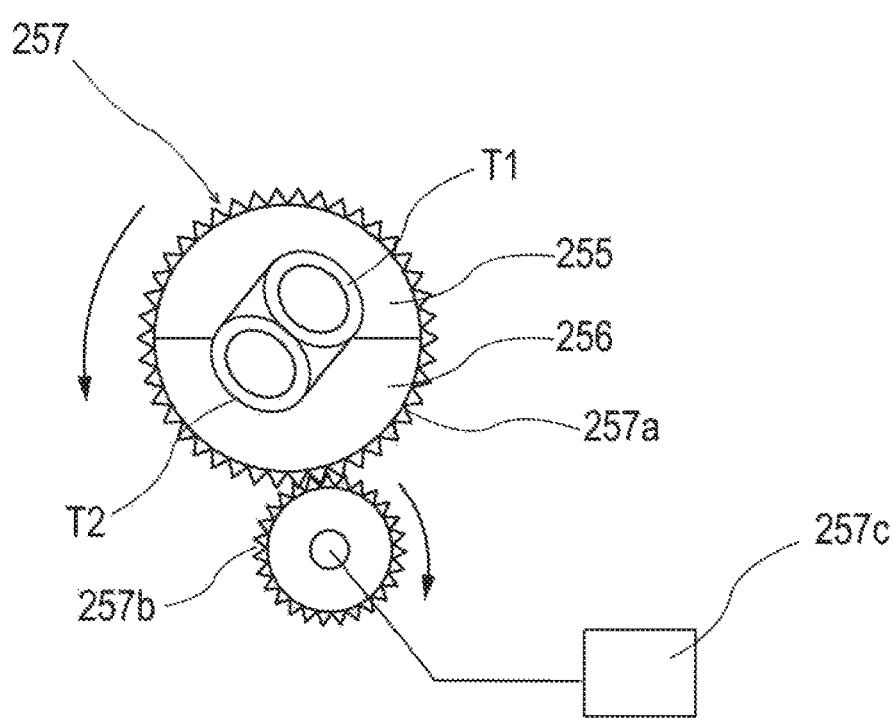
FIG. 8 is a schematic diagram showing a drive unit included in the tube pressing part.

As shown in FIG. 8, the drive unit 257 includes a first gear 257a provided around the lid-side clamp member 255 and the housing-side clamp member 256 integrated when the lid 22 is closed, a second gear 257b engaged with the first gear 257a, and a motor 257c connected to a rotating shaft of the second gear 257b.

When the controller 90 described later drives the motor 257c at a stage where cutting is completed, the second gear 257b rotates. The first gear 257a rotates with the rotation of the second gear 257b, so that the lid-side clamp member 255 and the housing-side clamp member 256 integrated also rotate with the first gear 257a. As a result, the lid-side pressing part 253 and the housing-side pressing part 254 continuous with the lid-side clamp member 255 and the housing-side clamp member 256 also rotate. As a result, as shown in FIG. 15D and FIG. 16A, the positions of the exchanged side X1 of the first tube T1 and the exchanged side X1 of the second tube T2 after cutting can be exchanged.

(Interlock)

The interlock 30 has a function of locking the clamp 20 in a state of sandwiching the first tube T1 and the second tube T2 during cutting and joining.

In the present embodiment, as shown in FIG. 12B, the interlock 30 is formed by an electromagnetically driven solenoid rod 31.

During cutting and joining, the solenoid rod 31 moves upward in the height direction Z of the housing 10 according to a command transmitted from the controller 90, and comes into contact with a front-side surface of the engaging claw 225 of the lid 22, keeping the grips 224 from rotating with respect to the clamp arms 221 and 222.

(Wafer Cassette Storage Unit)

The wafer cassette storage unit 40 has a function of storing the wafer cassette WC inserted into the housing 10, and a function of detecting the remaining quantity of wafers WF in the wafer cassette WC.

The wafer cassette storage unit 40 includes a storage for storing the wafer cassette WC inserted through the cassette insertion hole 11c, and a wafer remaining quantity detection sensor that can detect the remaining quantity of wafers WF in the wafer cassette WC (not shown). The wafer remaining quantity detection sensor can be formed, for example, by a known photosensor.

(Wafer Feed Unit)

The wafer feed unit 50 has a function of feeding a wafer WF to the cutting position, a function of heating a wafer WF for cutting, a function of cooling a used wafer WF, and a function of sending a used wafer WF to the outside of the housing 10.

The wafer feed unit 50 includes a drive unit that can feed a wafer WF from the wafer cassette WC in the wafer cassette storage unit 40 to the cutting position, and can send a used wafer WF to the outside of the housing 10 through the space 21a between the first pedestal 211 and the second pedestal 212, a heater that can heat a wafer WF for cutting, and a fan that can cool a used wafer WF (not shown).

(Operation Unit)

The operation unit 60 has a function of accepting instructions from the user M to the tube joining apparatus 1.

As shown in FIG. 1, the operation unit 60 is provided with a plurality of switches 61. By pressing the switches 61, the user M can make an instruction to the tube joining apparatus 1 to switch the power supply of the tube joining apparatus 1 on or off, an instruction to start cutting and joining, etc.

(Notification Unit)

The notification unit 70 has a function of notifying the user M of necessary information.

As shown in FIGS. 1 and 3, the notification unit 70 includes the display 71 that displays necessary information for the user M, and the speaker 72 that notifies the user M of necessary information by voice. The notification unit 70 is configured to be able to notify the user M that the power is ON, that charging is in progress, that cutting and joining is in progress, that the used wafer WF can be taken out, that the tube joining apparatus 1 is in failure, etc. Further, the notification unit 70 is configured to be able to notify the user M that the lid 22 is not closed when cutting and joining is performed, that the wafer cassette WC needs to be replaced, that the wafer WF is defective, that charging is required, that the temperature is inappropriate, etc.

(Power Supply)

The power supply 80 has a function of supplying power to the parts of the tube joining apparatus 1.

As shown in FIGS. 1 and 3, the power supply 80 includes a battery 81 that can supply power to the parts, and a charger 82 for charging the battery 81.

(Controller)

The controller 90 has a function of performing centralized control of the parts of the tube joining apparatus 1.

The controller 90 includes a CPU such as a microcomputer, ROM that stores control programs of the entire apparatus executed by the CPU and various data, and RAM that temporarily stores measurement data and various data as a work area.

Figure 13:
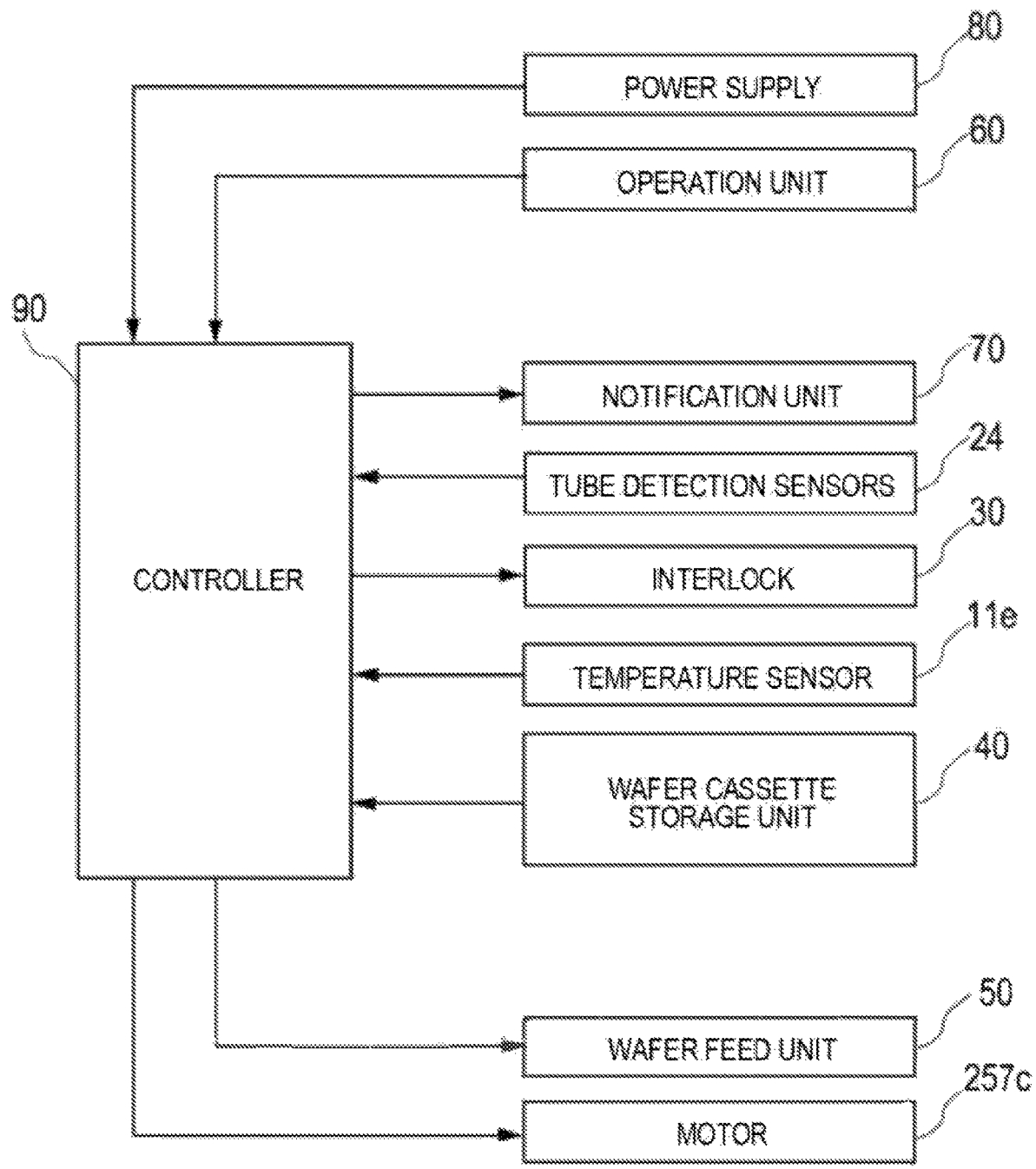
FIG. 13 is a block diagram showing a control system of the tube joining apparatus.

As shown in FIG. 13, the controller 90 is electrically connected to the power supply 80, and receives power supply from the power supply 80.

The controller 90 is electrically connected to the operation unit 60, and is configured to be able to control the operations of the parts in response to instructions from the user M.

The controller 90 is electrically connected to the notification unit 70, and is configured to be able to notify the user M of necessary information.

The controller 90 is electrically connected to the tube detection sensors 24, the interlock 30, and the temperature sensor 11e. For example, when the controller 90 obtains information from the tube detection sensors 24 that the first tube T1 and the second tube T2 are not properly set, the controller 90 can notify the information via the notification unit 70. The controller 90 is configured to keep the lid 22 in the closed position with the interlock 30 during cutting and joining. The controller 90 is configured to adjust time to heat the first tube T1 and the second tube T2 by the wafer WF during cutting, based on the ambient temperature of the housing 10 measured by the temperature sensor 11e.

The controller 90 is electrically connected to the wafer cassette storage unit 40 and the wafer feed unit 50, and is configured to be able to control their operations.

The controller 90 is electrically connected to the motor 257c of the movable-side pressing part 25b, and controls the position exchange operation of the movable-side pressing part 25b.

<Wafer Cassette>

As shown in FIG. 1, the wafer cassette WC stores a plurality of wafers WF. The wafer cassette WC is inserted and taken out through the cassette insertion hole 11c of the tube joining apparatus 1. As shown in FIG. 4A and FIG. 4B, a used wafer WF is taken out of the housing 10 from the space 21a between the first pedestal 211 and the second pedestal 212.

<Tubes>

Next, the first tube T1 and the second tube T2 joined by the tube joining apparatus 1 will be described.

In the present embodiment, the first tube T1 is formed by a tube on the peritoneal dialysate bag T11 side. Specifically, the predetermined connector T12 is attached to the distal end of the first tube T1. The opposite end of the first tube T1 is connected to a dialysate tube T14 of the dialysate bag T11 via a branch tube T13. Further, the first tube T1 is connected to a drain tube T16 of a drain bag T15 via the branch tube T13.

The second tube T2 is formed by a tube on the side of the peritoneal catheter T26 of the user M used for peritoneal dialysis. Specifically, the second tube T2 includes an extension tube T21 and a protection tube T22. The extension tube T21 is connected to the peritoneal catheter T26 via a connecting tube T23, a silicone tube T24, and a catheter joint T25. One end portion of the peritoneal catheter T26 is inserted into the abdominal cavity of the user M.

In the present embodiment, the first tube T1 and the second tube T2 are formed by polyvinyl chloride tubes. However, the material of the first tube T1 and the second tube T2 is not limited to that, and may be any as long as it allows the first and second tubes T1 and T2 to be joined to each other by cutting by melting and pressurization. For example, the first tube T1 and the second tube T2 may be of different materials.

<Example of Use>

Next, an example of using the tube joining set S will be described.

First, for using the tube joining apparatus 1, the user M inserts the wafer cassette WC into the cassette insertion hole 11c of the tube joining apparatus 1.

Next, as shown in FIG. 4A, the user M opens the lid 22 of the tube joining apparatus 1.

Next, as shown in FIG. 4B, the user M sets the first tube T1 and the second tube T2 in the predetermined positions of the holding parts 231, 232, and 233.

Next, the user M performs an operation to close the lid 22 (an operation to relatively move the lid 22 toward the housing 10). With this, as shown in FIG. 10A, the tube pressing part 25 sandwiches the first tube T1 and the second tube T2. When the lid 22 is further pushed down from the state of FIG. 10A, as shown in FIG. 11B, the protrusion 234b of the third holding part 233 of the tube holding part 23 comes into contact with the flat surface 234a of the lid 22. When the lid 22 is further pushed down from the state of FIG. 11B to completely close the lid 22, as shown in FIG. 12B, the third holding part 233 retracts from the holding position P0 to the release position P1, releasing the holding of the tubes T1 and T2. By the lid 22 being closed, outer peripheral portions of the cut parts of the first tube T1 and the second tube T2 are covered by the cover 223 and isolated from the outside. This allows the cutting and joining operation to be performed under aseptic conditions.

Next, the user M operates the operation unit 60 to instruct the tube joining apparatus 1 to start cutting and joining. Then, the controller 90 starts the cutting and joining operation.

First, the controller 90 activates the interlock 30 to lock the lid 22 in the closed position.

Next, the controller 90 controls the operation of the wafer feed unit 50 to perform a cutting operation. Specifically, as shown in FIG. 15C, a heated wafer WF is fed from the wafer cassette WC, and passes through a space between the fixed-side pressing part 25a and the movable-side pressing part 25b, cutting the first tube T1 and the second tube T2 by melting.

Next, the controller 90 drives the motor 257c of the movable-side pressing part 25b to exchange the positions of the exchanged side X1 of the first tube T1 and the exchanged side X1 of the second tube T2 as shown in FIG. 15D. Thereafter, as shown in FIG. 16A, the ends of the first tube T1 and the second tube T2 exchanged in positions are brought closer to each other and pressure-joined.

Next, the controller 90 unlocks the interlock 30.

Next, the user M performs an operation to open the lid 22 and removes the tubes T1 and T2 from the tube joining apparatus 1. When the joining is completed, the first tube T1 and the second tube T2 are joined in an X shape as shown in FIG. 16B. Thus, the user M performs an operation to separate the first tube T1 and the second tube T2 joined, into two tubes. Consequently, as shown in FIG. 16C, a tube with the fixed side X2 of the first tube T1 (the side connected to the connector T12) joined to the exchanged side X1 of the second tube T2 (the side of the end to which nothing is connected), and a tube with the exchanged side X1 of the first tube T1 (the side connected to the branch tube T13) joined to the fixed side X2 of the second tube T2 (the side connected to the peritoneal catheter T26) are obtained.

As above, the tube joining apparatus 1 according to the present embodiment includes the housing 10, the lid 22 relatively movable toward and away from the housing 10, the tube holding part 23 that holds the first tube T1 and the second tube T2 individually in the state of being placed side by side in the oblique direction D1 with respect to the height direction Z of the housing 10, and the tube pressing part 25 that presses the first tube T1 and the second tube T2 against each other as the lid 22 relatively moves toward the housing 10.

Consequently, the user M can set the tubes T1 and T2 individually while visually checking the disposed positions of the tubes T1 and T2 in the tube holding part 23, and can suitably visually check whether the tubes are set properly. Thus, it is not necessary to place the tubes T1 and T2 on each other in setting them. Whether the tubes T1 and T2 are properly set in the tube holding part 23 can be visually checked suitably. Consequently, it is possible to suitably prevent occurrence of setting errors of the tubes T1 and T2 such as twists in the tubes T1 and T2.

The tube holding part 23 holds the first tube T1 disposed on the back side in the direction D1 in which the first tube T1 and the second tube T2 are placed side by side, in a position higher than that of the second tube T2 in the height direction Z of the housing 10. Therefore, the user M can suitably visually check the first tube T1 set on the back side.

The tube holding part 23 includes the recessed grooves 231*a*, 232*a*, and 233*c* into which the first tube T1 can be fitted, and the recessed grooves 231*b*, 232*b*, and 233*d* into which the second tube T2 can be fitted. This allows the user M to set the tubes T1 and T2 individually by inserting them into the grooves.

The tube pressing part 25 presses the first tube T1 and the second tube T2 against each other along the oblique direction D1 in which the first tube T1 and the second tube T2 are placed side by side, as the lid 22 relatively moves toward the housing 10. This allows the tubes T1 and T2 set by the user M to be flattened only by slightly moving them closer. Since there is no need to largely move the set tubes T1 and T2, it is possible to give the user M a sense of security that the first tube T1 and the second tube T2 can be pressed against each other by closing the lid 22.

The tube holding part 23 holds the first tube T1 and the second tube T2 such that the imaginary line connecting the axis of the first tube T1 and the axis of the second tube T2 forms an angle of 45° with respect to the height direction Z of the housing 10. This allows the first tube T1 and the second tube T2 to be set in the positions where the user M can more easily visually check both the first tube T1 and the second tube T2.

Although the tube joining apparatus according to the present invention has been described above through the embodiment, the present invention is not limited to the configuration described in the embodiment, and can be modified appropriately based on the description of the scope of the claims.

For example, the above embodiment has described a form in which the first tube is a dialysate tube connected to a peritoneal dialysate bag via a branch tube, and the second tube is a tube on the side of a peritoneal catheter of a patient used for peritoneal dialysis. However, the tubes are not limited to particular ones as long as they are tubes exchanged in end positions after cutting and pressure-joined. For example, the first tube may be a tube that is connected to a plurality of peritoneal dialysate bags and drain tanks and connected to an apparatus that automatically performs peritoneal fluid dialysis. The first tube and the second tube are not limited to tubes used for peritoneal dialysis.

For example, in the above-described embodiment, the first tube is disposed on the back side and the second tube is disposed on the front side, but the first tube may be disposed on the front side and the second tube may be disposed on the back side.

For example, the above-described embodiment has described a form in which the legs provided at the bottom surface of the housing are in contact with a placement place such as a table. However, for example, the bottom surface of the housing may not be provided with legs, and the bottom surface may be in direct contact with a placement place such as a table.

For example, the above-described embodiment has described a form in which the tube holding part includes the first holding part, the second holding part, and the third holding part. However, the number of holding parts of the tube holding part is not limited to a particular number.

This application is based on Japanese Patent Application No. 2017-142857 filed on Jul. 24, 2017, the disclosure of which is incorporated herein by reference in its entirety.

The invention claimed is:

1. A tube joining apparatus that melts and cuts an end portion of a first tube and an end portion of a second tube with a heated plate-shaped cutting member, and then exchanges positions of the cut end portion of the first tube and the cut end portion of the second tube and joins the tubes under aseptic conditions, the apparatus comprising:
a housing;
a lid relatively movable toward and away from the housing;
a tube holding part that holds the first tube and the second tube individually in a state of being placed side by side in an oblique direction with respect to a height direction of the housing; and
a tube pressing part that presses the first tube and the second tube against each other as the lid relatively moves toward the housing.

2. The tube joining apparatus according to claim 1, wherein the tube holding part holds one of the first tube and the second tube disposed on a back side of the tube holding part in the oblique direction in which the first tube and the second tube are placed side by side, in a position higher than a position of the other tube in the height direction of the housing.

3. The tube joining apparatus according to claim 2, wherein the tube holding part comprises a recessed groove into which the first tube can be fitted, and a recessed groove into which the second tube can be fitted.

4. The tube joining apparatus according to claim 1, wherein the tube pressing part presses the first tube and the second tube against each other along the oblique direction in which the first tube and the second tube are placed side by side as the lid relatively moves toward the housing.

5. The tube joining apparatus according to claim 1, wherein the tube holding part holds the first tube and the second tube such that an imaginary line connecting an axis of the first tube and an axis of the second tube forms an angle of 45° with respect to the height direction of the housing.

6. The tube joining apparatus according to claim 1 wherein the tube holding part holds the first tube and the second tube such that an imaginary line connecting an axis of the first tube and an axis of the second tube forms an angle of greater than or equal to 30° and less than or equal to 45° with respect to the height direction of the housing.

7. The tube joining apparatus according to claim 1 wherein the tube holding part comprises a first pedestal mounted on said housing and a first clamp part mounted on said first pedestal, said first clamp part having first and second parallel grooves for receiving said first and second tubes and a first housing side pressing part and a second pedestal mounted on said housing adjacent said first pedestal, thereby forming a space for receiving said cutting member, and a second clamp part mounted on said second pedestal, said second clamp part comprising a second housing side pressing part, and a first lid-side pressing part mounted on said lid and contacting said first housing side pressing part when said lid is moved toward said housing and a second lid-side pressing part mounted on said lid and contacting said second housing side pressing part when said lid is moved toward said housing.

8. The tube joining apparatus according to claim 7, wherein said parallel grooves of said first clamp part hold the first tube and the second tube such that an imaginary line connecting an axis of the first tube and an axis of the second tube forms an acute angle with respect to the height direction of the housing.

9. The tube joining apparatus according to claim 8 wherein said angle is greater than or equal to 30° and less than or equal to 45° with respect to the height direction of the housing.

10. The tube joining apparatus according to claim 7 further comprising means for rotating said second clamp part.

11. The tube joining apparatus according to claim 10 further comprising control means for activating said means for rotating after said first and second tubes are pressed against each other and cut by said tube joining apparatus.

12. The tube joining apparatus according to claim 7 wherein said lid comprises a first clamp arm pivotally attached to said first pedestal and a second clamp arm pivotally attached to said second pedestal.

13. The tube joining apparatus according to claim 12 wherein first lid-side pressing part protrudes from said first clamp arm into said space for receiving said cutting member and said first housing side pressing part protrudes from said first pedestal into said space for receiving said cutting member.

14. The tube joining apparatus according to claim 12 wherein second lid-side pressing part protrudes from said second clamp arm into said space for receiving said cutting member and said second housing side pressing part protrudes from said second pedestal into said space for receiving said cutting member.

15. The tube joining apparatus according to claim 7 further comprising a movable holding part pivotally attached to said second pedestal, said holding part having a first notch coaxially aligned with said first groove and a second notch coaxially aligned with said second groove when said lid is in an open position.

16. The tube joining apparatus according to claim 15 further comprising means for disconnecting said movable holding part from said first and second tubes when said lid is moved toward said housing.

* * * * *